United States Patent [19]

Goto et al.

[11] Patent Number: 5,177,087
[45] Date of Patent: Jan. 5, 1993

[54] CYCLIC AMINE COMPOUNDS AND THEIR USE

[75] Inventors: Giichi Goto, Toyono; Hidefumi Yukimasa, Nara; Tetsuji Imamoto, Katsuragi, all of Japan

[73] Assignee: Takeda Chemical Industries, Ltd., Osaka, Japan

[21] Appl. No.: 461,114

[22] Filed: Jan. 4, 1990

[30] Foreign Application Priority Data

Jan. 13, 1989 [JP] Japan .................. 1-6651
Jul. 12, 1989 [JP] Japan .................. 1-179495
Sep. 28, 1989 [JP] Japan .................. 1-253162

[51] Int. Cl.$^5$ ............... A61K 31/445; C07D 211/26
[52] U.S. Cl. ..................... 514/331; 514/212; 514/255; 514/316; 514/318; 514/326; 540/597; 544/360; 546/187; 546/193; 546/208; 546/229
[58] Field of Search ............ 546/229, 187, 193, 208; 514/331

[56] References Cited

U.S. PATENT DOCUMENTS 2,686,784 8/1954 Finkelstein .............. 546/229
3,632,767 1/1972 Gray et al. .............. 546/229

FOREIGN PATENT DOCUMENTS 0229391 7/1987 European Pat. Off. .
0296560 12/1988 European Pat. Off. .
0320983 6/1989 European Pat. Off. .
0012643 6/1980 France .

Primary Examiner—C. Warren Ivy
Assistant Examiner—Celia Chang
Attorney, Agent, or Firm—Wegner, Cantor, Mueller & Player

[57] ABSTRACT

There is provided a cyclic amine compound of the formula

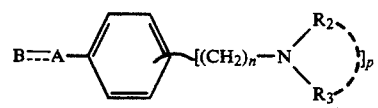

wherein B means a saturated or unsaturated 5- to 7-membered aza-heterocyclic group which may be substituted; A means a bond or an alkylene or alkenylene group which may be substituted by hydrocarbon residues, oxo, hydroxyimino, and/or hydroxy, ≡≡≡ means either a single bond or a double bond (provided that when A means a bond, ≡≡≡ means a single bond); $R_2$ and $R_3$ independently mean a hydrogen atom or a hydrocarbon residue which may be substituted (provided that both of $R_2$ and $R_3$ are not hydrogen atoms) or jointly form a cyclic amino group together with the adjacent nitrogen atom, n is 0, 1 or 2 and p is 1 or 2 or a physiologically acceptable salt thereof.

The compounds are useful for therapy of cerebral edema, acute symptoms in cerebral apoplexy and protection of brain and nerve cell, or useful as anticholinesterase or as brain function-improving agent.

12 Claims, No Drawings

CYCLIC AMINE COMPOUNDS AND THEIR USE

An present invention relates to pharmaceutical agents and more particularly to novel cyclic amine compounds which are effective in treating various symptoms due to brain hypoxia or ischemia, particularly cerebral edema.

The current therapeutic modality for the cerebral edema associated with increased intracranial pressure due to compression by a brain neoplasm or trauma or that associated with cerebral ischemia comprises a massive administration of corticosteroids and the ethylene glycol therapy utilizing its osmotic pressure but no therapeutic drug is available that is satisfactory in efficacy or in the aspect of side effects.

The object of the present invention is to provide a novel class of compounds which are useful as therapeutic drugs for cerebral edema.

The invention provides compounds useful as medicaments for improving the functions of the central nervous system and particularly compounds of value for the relief of cerebral edema due to brain ischemia of the formula

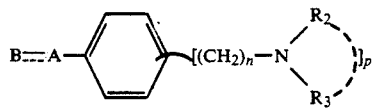

wherein B means a saturated or unsaturated 5- to 7-membered aza-heterocyclic group which may be substituted; A means a bond or a two- or three-valent aliphatic hydrocarbon residue which may be substituted by hydrocarbon residues, oxo, hydroxyimino and/or hydroxy; ==== means either a single bond or a double bond (provided that when A means a bond, ==== means a single bond); $R_2$ and $R_3$ independently mean a hydrogen atom or a hydrocarbon residue which may be substituted (provided that both of $R_2$ and $R_3$ are not hydrogen atoms) or jointly form a cyclic amino group together with the adjacent nitrogen atom; n is 0, 1 or 2; and p is 1 or 2 [hereinafter referred to sometimes as compound (I)] and salts thereof. It was found that these compounds and salts have very potent ameliorative effects on cerebral edema. Accordingly, the inventors conducted further research and accomplished the present invention.

The present invention is, therefore, directed, in one aspect, to a cyclic amine compound of formula (I) as well as a salt thereof and, in another aspect, to a therapeutic agent for cerebral edema, acute symptoms in cerebral apoplexy or stroke and a brain/nerve cell protecting agent, both containing said compound or salt. It has been further found that among various species of compound (I), the compounds in which B is a 5- to 7-membered aza-heterocyclic group substituted by a benzyl group (which itself may be substituted) in the N-position additionally have potent anticholinesterase activity.

In the aspect of the therapy of cerebral edema, disturbance of microcirculation in the brain (e.g. increase in erythrocyte deformability) and acute symptoms in cerebral apoplexy and a protection of neuronal cell death or cholinesterase inhibitory action, among the compounds (I), particularly preferred are the compounds of the formula

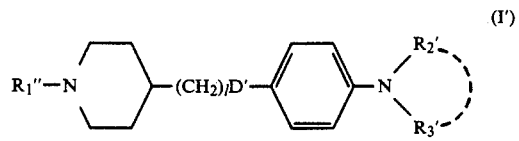

wherein $R_1''$ is a hydrogen atom or a benzyl group which may be substituted, l is an integer of 0 to 4 and D' is a group of the formula

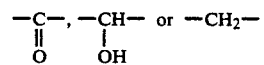

and $R_2'$ and $R_3'$ are independently a $C_{1-6}$alkyl group or jointly form a cyclic amino group together with the adjacent nitrogen atom [hereinafter referred to sometimes as compound (I')] and salts thereof.

Referring, now, to formula (I), the "saturated or unsaturated 5- to 7-membered aza-heterocyclic group which may be substituted", denoted by B, includes various nitrogen-containing 5- to 7-membered heterocycles, saturated and unsaturated. Particularly desirable heterocycles include, among others, saturated or unsaturated 5- through 7-membered heterocycles each containing one nitrogen atom such as those represented by the formula

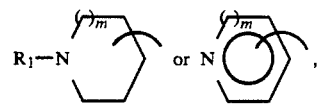

wherein $R_1$ is a hydrogen atom, a hydrocarbon residue which may be substituted or an acyl group which may be substituted and m is 0, 1 or 2. Furthermore, among various heterocyclic groups which may be chosen for B, one which is bound to —A— in a position other than the N-positin of the ring, that is to say a carbon position, is preferred. Hereinafter, the saturated and unsaturated rings mentioned above will sometimes be designated by the formula

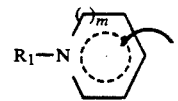

In this connection, $R_1$ means said hydrogen atom, hydrocarbon residue which may be substituted or acyl group which may be substituted only when the ring is attached to —A— in a position other than the N-position, that is to say in a carbon position, and is either saturated or partially unsaturated without involvement of N.

Referring to $R_1''$ in the formula (I'), $R_1''$ is a hydrogen atom or a benzyl group among the definition of R.

The hydrocarbon residue of the "hydrocarbon residue which may be substituted" as denoted by $R_1$, $R_2$ and $R_3$ and that as a substituent group on the "alkylene or alkenylene group which may be substituted by hydrocarbon residues, oxo and/or hydroxy" as denoted by A includes, among others, $C_{1-6}$ alkyl groups (e.g. methyl, ethyl, propyl, butyl, hexyl, 4-methylpentyl, etc.), $C_{2-4}$ alkenyl groups such as vinyl, allyl, 2-butenyl, etc., $C_{2-4}$ alkynyl groups such as propargyl, 2-butynyl, etc., aryl groups such as phenyl, naphthyl, etc., and aralkyl groups such as benzyl, diphenylmethyl, phenylethyl, naphthylmethyl and naphthylethyl. The aryl or aralkyl group (including the benzyl group, as denoted by $R_1''$) for $R_1$, $R_2$ and $R_3$ may have 1 to 3 substituents on the ring, such as, for example, $C_{1-3}$ alkoxy groups (e.g. methoxy, ethoxy), $C_{1-3}$ alkyl groups (e.g. methyl, ethyl, propyl), cyano, amino, mono- or di-$C_{1-6}$alkylamino; 5- to 7-membered cyclic amino, hydroxy, nitro, halogens (e.g. chlorine, fluorine, bromine) and so on. The alkyl moiety of said aralkyl group may be substituted by oxo or hydroxy.

The substituent groups which may substitue the alkyl, alkenyl and alkynyl groups mentioned for $R_1$, $R_2$ and $R_3$ include, among others, the above-mentioned halogen, $C_{1-3}$ alkoxy cyano, amino, mono- or di-$C_{1-6}$ alkylamino, 5- to 7-membered cyclic amino and hydroxy.

The acyl moiety of "the acyl group which may be substituted", denoted by $R_1$, includes carboxylic acid acyl groups (e.g. $C_{2-6}$ alkylcarbonyl groups such as acetyl, propionyl, butyryl, etc.) and substituted oxycarbonyl groups (e.g. $C_{2-8}$ alkyl- or aralkyloxycarbonyl groups such as methoxycarbonyl, tert-butoxycarbonyl, benzyloxycarbonyl, etc.), for instance.

The substituent groups which may substitute such acyl groups include, among others, halogens (e.g. iodine, bromine, fluorine, chlorine), amino, and primary or secondary amino having $C_{1-6}$ alkyl substituents (e.g. methyl, ethyl, propyl, hexyl). The acyl groups may respectively have 1 to 3, preferably 1 to 2, such substituents.

The cyclic amino group which is formed by $R_2$ and $R_3$, and $R_2'$ and $R_3'$ together with the adjacent nitrogen atom includes various nitrogen-containing 5- through 7-membered heterocyclic groups, such as those of the formula

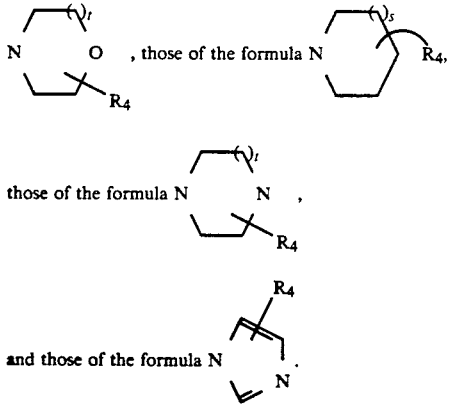

In the above formulas, s is 0, 1 or 2, t is 1 or 2; $R_4$ is a hydrogen atom or a substituent group which may substitute the cyclic amino group formed by $R_2$ and $R_3$, which substituent group may for example be $C_{1-3}$ alkyl (e.g. methyl, ethyl, propyl), $C_{1-3}$ alkylcarbonyl (e.g. acetyl, propionyl, butyryl), oxo, hydroxy, phenyl, benzyl, diphenylmethyl or amino. The "two- or three-valent hydrocarbon residue which may be substituted by hydrocarbon residues, oxo, hydroxyimino or/and hydroxy" which is denoted by A is preferably exemplified by $C_{1-6}$-alkylene or -alkenylene chains and methine. Examples of A include

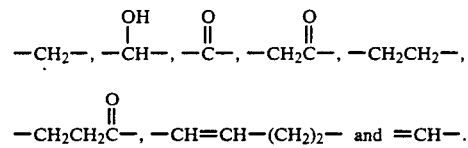

Preferred types of compound (I) include the following, for instance.

$R_1$ is preferably a hydrogen atom, a $C_{1-4}$ alkyl group or a benzyl group which may be substituted, and more desirably a hydrogen atom, a $C_{1-2}$ alkyl group or a benzyl group which may be substituted. Compounds in which $R_1$ is a benzyl group tend to be superior in terms of anticholinesterase activity and those in which $R_1$ is a hydrogen atom or an alkyl group tend to be superior in terms of therapeutic efficacy for cerebral edema. Preferably, $R_1$ and $R_3$ independently mean a $C_{1-4}$ alkyl group or phenylmethyl, or jointly constitute a cyclic amino group together with the adjacent nitrogen atom. More desirably, $R_2$ and $R_3$ independently mean a $C_{1-3}$ alkyl group or a group of the formula

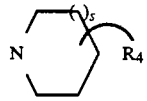

where s is 0, 1 or 2 and $R_4$ means hydrogen, phenyl or benzyl. Preferably, B is piperidyl, pyrrolidyl, pyrrolyl or pyridyl. Particularly preferred is piperidyl. Preferably, A is hydroxymethylene, a group of the formula $$\left(\begin{array}{c} R_5 \\ | \\ C \\ | \\ R_6 \end{array}\right)_q$$

(where $R_5$ and $R_6$ respectively mean a hydrogen atom or a $C_{1-3}$ alkyl group; q is 1 or 2; and the total number of carbon atoms is not more than 6) or a group of the formula

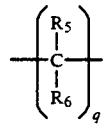

(wherein l is an integer of 0 to 4; this group is attached to the benzene ring through $$-\underset{\underset{O}{\|}}{C}-).$$

More desirably, A is methylene, hydroxymethylene or $$-CH_2CH_2\underset{\underset{O}{\|}}{C}-.$$

Preferably, m is 1 or 2, and more desirably, m is 1. Preferably, n is 0 or 1, and more desirably. n is 0.

Particularly the compounds in which B is an N-benzyl-substituted piperidinyl group are satisfactory in anticholinesterase activity.

The more desirable compounds, in terms of anticholinesterase activity, are compounds of the formula (I) wherein $R_1''$ is a benzyl group and D' is —CO—, that is, compounds of the formula

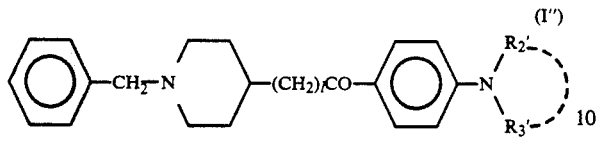

wherein l, $R_2'$ and $R_3'$ are as defined hereinbefore [hereinafter referred to as compound (I")] and the salts thereof.

In the aspect of the therapy of cerebral edema, disturbance of microcirculation in the brain (e.g. increase in erythrocyte deformability) and acute symptoms in cerebral apoplexy or stroke, and a protection of neuronal cell death and the like, more preferable are compounds of the formula (I') wherein $R_1''$ is a hydrogen atom and l is 0, that is, compounds of the formula

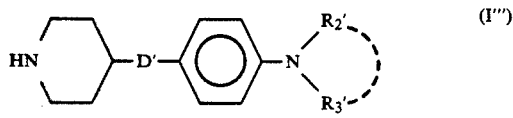

[hereinafter referred to as compound (I''')] wherein D' $R_2'$ and $R_3'$ are as defined above, and the salts thereof.

Particularly, the compounds of the formula (I') wherein $R_1''$ is a hydrogen atom, l is 0 and D' is —CH$_2$—, and the salts thereof are particularly useful in terms of therapeutic efficacy for cerebral edema and acute symptoms in stroke.

The compound according to the present invention may be provided not only as the compounds of the formula (I) but also in the form of an acid addition salts, thereof particularly a physiologically acceptable acid addition salt. Examples of such acid addition salt include inorganic acid salts (e.g. salts with hydrochloric acid, sulfuric acid, nitric acid, phosphoric acid, hydrobromic acid) and organic acid salts (e.g. salts with acetic acid, propionic acid, fumaric acid, maleic acid, tartaric acid, citric acid, malic acid, oxalic acid, benzoic acid, methanesulfonic acid, benzenesulfonic acid).

The processes for production of the compound of the present invention are described below.

Among the specific compounds of formula (I) according to the present invention, compounds of the formula

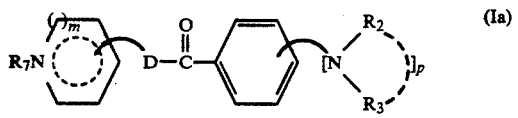

wherein $R_7$ means a substituent group in the N-position when the

ring is saturated, and means an acyl group which may be substituted, which is included in the definition of $R_1$;

D means either a bond or an $C_{1-5}$ alkylene group which may be substituted by hydrocarbon residues, oxo or-/and hydroxy; $R_2$, $R_3$, m and p are respectively as defined hereinbefore [these compounds are collectively referred to as compound (Ia)] can each be produced by reacting, for example, a compound of formula (II)

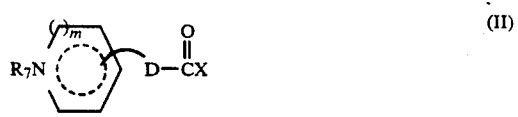

wherein D, $R_7$ and m are respectively as defined hereinbefore and X means a halogen (e.g. chlorine, bromine, iodine) with, for example, a compound of formula (III)

wherein p is as defined hereinbefore and Y means a halogen atom (e.g. fluorine, chlorine, bromine, iodine) to give a compound of formula (IV)

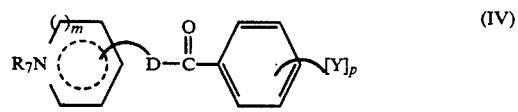

wherein D, $R_7$, Y, m and p are respectively as defined above and, then, reacting this compound of formula (IV) with, for example, a compound of formula (V)

wherein $R_2$ and $R_3$ are as defined hereinbefore.

The compound of formula (II) can be prepared by a known method or a method analogous thereto. For example, compound (II) can be prepared in accordance with the process described in Chemical Pharmaceutical Bulletin 34, 3747-3761, 1986.

The reaction between compound (II) and compound (III) can be carried out by a per se known method. For example, compound (II) is reacted with compound (III), either in the absence of a solvent or in a solvent, if necessary in the presence of an acid or the like. The acid may be a Lewis acid such as aluminum chloride, zinc chlorine, titanium chloride or the like. The solvent may be any of the common solvents unless it interferes with the reaction. Thus, for example, the reaction can be conducted in dichloromethane, dichloroethane, nitrobenzene, carbon disulfide or the like at a temperature of generally about −30° C. to 150° C. and preferably about 20° to 100° C. To each mole of compound (II), compound (III) is generally used in a proportion of about 1 to 20 moles, preferably about 2 to 5 moles. The reaction between compound (IV) and compound (V) can also be conducted by a per se known method. For example, compound (IV) is reacted with compound (V), either in the absence of a solvent or in a solvent, at a temperature of about −50° C. to 300° C., preferably about 20° to 200° C. The solvent may be any of the common solvents, such as water, methanol, ethanol, propanol, chloroform, dichloromethane, benzene, toluene, xylene, acetonitrile, dimethylformamide, N-methylpyrrolidone, dimethyl sulfoxide and so on. If necessary, this reaction can be conducted in the presence of an organic base, such as pyridine, 4-dimethylaminopyridine, triethylamine, triethylenediamine, tetramethylethylenediamine, etc., an inorganic base, such as sodium hydrogen carbonate, potassium hydrogen carbonate, sodium carbonate, potassium carbonate, sodium hydroxide, potassium hydroxide, etc., sodium hydride, potassium hydride and so on.

To each mole of compound (IV), compound (V) is used in a proportion of generally about 1 to 10 moles and preferably about 2 to 4 moles. The reaction time is generally about 1 to 48 hours and preferably about 10 to 20 hours.

Among various species of compound (I), compounds of formula (Ib)

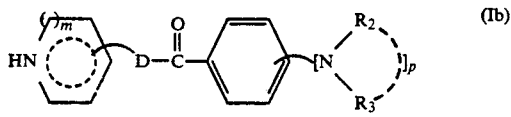

wherein D, R$_2$, R$_3$, m and p are respectively as defined hereinbefore, provided that the hydrogen atom in the N-position of ring

is available only when the ring is saturated, can each be prepared by treating the above-mentioned compound (Ia) with an acid or a base. Thus, compound (Ia) is treated in an aqueous solution of mineral acid (e.g. nitric acid, hydrochloric acid, hydrobromic acid, iodic acid, sulfuric acid, etc.) or an aqueous solution of alkali metal hydroxide (e.g. sodium hydroxide, potassium hydroxide, barium hydroxide, lithium hydroxide, etc.) at a temperature of generally 10° to 150° C. and preferably 50° to 100° C. Generally 10 to 100 equivalents, preferably 20 to 40 equivalents, of the acid or base is used relative to compound (Ia). The strength of the acid or base is preferably about 1 to 10N and preferably about 4 to 10N. Though it depends on reaction temperature, the reaction time is generally about 1 to 24 hours and preferably about 2 to 10 hours.

The compounds of formula (Ic)

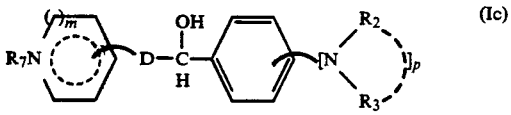

wherein D, R$_2$, R$_3$, R$_7$, m and p are respectively as defined hereinbefore can each be prepared by reducing a compound of formula (Ia) by a per se known procedure. For example, compound (Ia) is subjected to catalytic reduction in a solvent using hydrogen in the presence of a catalyst. The solvent may be any of the common solvents for chemical reactions unless the intended reaction is adversely affected. Thus, for example, the reaction can be conducted in water, methanol, ethanol, dimethylformamide, tetrahydrofuran, dioxane or the like with the aid of a palladium, rhodium, platinum, Raney nickel or other catalyst at a temperature of generally about −10° C. to 100° C. and preferably about 20° to 50° C., at a hydrogen pressure of 1 to 100 atmospheres, preferably 1 to 5 atmospheres, if necessary in the presence of an acid. The acid may be a mineral acid (e.g. hydrochloric acid, nitric acid, phosphoric acid, hydrobromic acid) or an organic acid (e.g. acetic acid, propionic acid, tartaric acid, benzoic acid, methanesulfonic acid, toluenesulfonic acid, etc.). The compound (Ic) can also be produced by treating compound (Ia) with a metal hydride (e.g. diisobutylaluminum hydride, triphenyltin hydride, etc.), a metal hydrogen complex compound (e.g. lithium aluminum hydride, sodium aluminum hydride, sodium triethoxyaluminum hydride, etc.), diborane or a substituted borane (e.g. sodium borohydride). These metal hydride compounds are used in a proportion of generally 0.3 to 5 moles and preferably 1 to 2 moles per mole of compound (Ia). The solvent may be any of the common solvents for chemical reactions unless it interferes with the intended reaction. Thus, for example, the reaction can be carried out in a protic solvent (e.g. water, methanol, ethanol, propanol, etc.) or an aprotic solvent (e.g. ethyl ether, tetrahydrofuran, dioxane, etc.) at a temperature of −10° C. to 200° C., preferably 20° to 100° C.

Compounds of formula (Id)

Compounds of formula (Id)

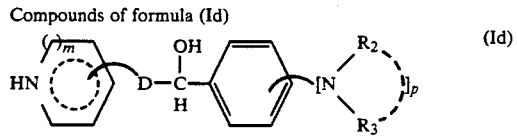

wherein D, R$_2$, R$_3$, m and p are respectively as defined hereinbefore can each be produced by treating a compound of formula (Ic) with an acid or a base or by reducing a compound of formula (Ib) by a per se known procedure. The acid or base which can be used in the above treatment of compound (Ic) includes mineral acids (e.g. nitric acid, hydrochloric acid, hydrobromic acid, iodic acid, sulfuric acid, etc.) and alkali metal hydroxides (e.g. sodium hydroxide, potassium hydroxide, barium hydroxide, lithium hydroxide, etc.). This treatment can be carried out in an aqueous solution of the acid or base at a temperature of 10° to 150°, preferably 50° to 100° C. The strength of the acid or base is generally about 1 to 10N and preferably 4 to 10N. Based on compound (Ic), the acid or base is generally used in a proportion of about 20 to 40 equivalents. Though it depends on the reaction temperature used, the reaction time is generally about 1 to 24 hours and preferably about 2 to 10 hours. Regarding the above mentioned per se known procedure for reducing compound (Ib), the solvent may be any of the solvents commonly used for chemical reactions unless it interferes with the intended reaction. Thus, for example, water, methanol, ethanol, dimethylformamide, tetrahydrofuran, dioxane, etc. can be mentioned. The catalyst may for example be a palladium, rhodium, platinum or Raney nickel catalyst. The reaction can be conducted in the presence of such catalyst at a temperature of about −10° C. to 100° C., preferably about 20° to 50° C., under the hydrogen pressure of 1 to 100 atmospheres, preferably 1 to 5 atmospheres, if necessary in the presence of an acid. The acid may be a mineral acid (e.g. hydrochloric acid, nitric acid, phosphoric acid, hydrobromic acid, etc.) or an organic acid (e.g. acetic acid, propionic acid, tartaric acid, benzoic acid, methanesulfonic acid, toluenesulfonic acid, etc.), for instance. The compound (Id) can also be produced by treating compound (Ib) with a metal hydride (e.g. diisobutylaluminum hydride, triphenyltin hydride, etc.), a metal hydrogen complex compound (e.g. lithium aluminum hydride, sodium aluminum hydride, sodium triethoxyaluminum hydride), diborane or a substituted borane (e.g. sodium borohydride, etc.) in a solvent. The solvent may be any of the common solvents for chemical reactions unless it interferes with the intended reaction. Thus, this treatment can be carried out in a protic solvent (e.g. water, methanol, ethanol, propanol, etc.) or an aprotic solvent (e.g ethyl ether, tetrahydrofuran, dioxane, etc.) at a temperature of generally $-10°$ C. to $200°$ C. and preferably $20°$ to $100°$ C.

Compounds of formula (Ie)

Compounds of formula (Ie)

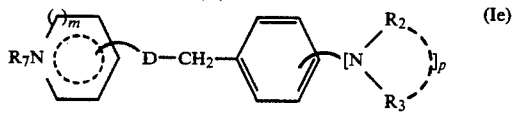

wherein D, $R_2$, $R_3$, $R_7$, m and p are as defined hereinbefore can each be produced by reducing a compound of formula (Ia) or (Ic). The solvent to be used for this reaction may be any of the common solvents for chemical reactions unless it interferes with the reaction. Thus, for example, water, methanol, ethanol, dimethylformamide, tetrahydrofuran and dioxane may be mentioned. The reaction can be conducted in such a solvent with the aid of a catalyst, which may be a palladium, rhodium, platinum or Raney nickel catalyst, at a temperature of generally about $-10°$ C. to $100°$ C. and preferably about $20°$ to $50°$ C., under the hydrogen pressure of 1 to 100 atmospheres, preferably 1 to 5 atmospheres, if necessary in the presence of an acid. The acid may be a mineral acid (e.g. hydrochloric acid, nitric acid, phosphoric acid, hydrobromic acid) or an organic acid (e.g. acetic acid, propionic acid, tartaric acid, benzoic acid, methanesulfonic acid).

Compounds of formula (If)

Compounds of formula (If)

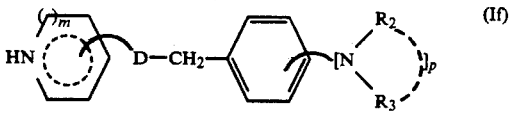

wherein D, $R_2$, $R_3$, m and p are respectively as defined hereinbefore can each be produced by treating compound (Ie) with an acid or a base. Thus, compound (Ie) is treated with a mineral acid (e.g. nitric acid, hydrochloric acid, hydrobromic acid, iodic acid, sulfuric acid, etc.) or an alkali metal hydroxide (e.g. sodium hydroxide, potassium hydroxide, barium hydroxide, lithium hydroxide, etc.) at a temperature of generally $10°$ to $150°$ C. and preferably $50°$ to $100°$ C. The strength of the acid or base is generally about 1 to 10N and preferably about 4 to 10N. Though it depends on reaction temperature, the reaction time is generally about 1 to 24 hours and preferably about 2 to 10 hours.

Compounds of formula (Ig)

Compounds of formula (Ig)

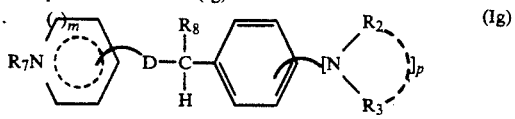

wherein D, $R_2$, $R_3$, $R_7$, m and p are respectively as defined hereinbefore, and $R_8$ has the same meaning as defined for $R_5$ and $R_6$, namely a hydrogen atom, a hydroxy group or a $C_{1-3}$ alkyl group, can be produced by reacting a compound of formula (Ia) with a compound of formula (VI)

$$R_8MgZ \qquad (VI)$$

wherein $R_8$ is as defined above and Z means a halogen atom (e.g. chlorine, bromine, iodine) and subjecting the reaction product to catalytic reduction with hydrogen in the presence of a catalyst. The reaction between compound (Ia) and compound (VI) can be conducted in an aprotic solvent such as tetrahydrofuran, ethyl ether, isopropyl ether, dimethoxyethane, benzene or the like at a temperature of generally about $-50°$ C. to $100°$ C. and preferably about $0°$ to $50°$ C. The catalytic reduction with hydrogen can be carried out in a solvent, such as water, methanol, ethanol, dimethylformamide, tetrahydrofuran, dioxane or the like, in the presence of a catalyst, which may for example be a palladium catalyst, rhodium catalyst or Raney nickel catalyst, at a temperature of about $-10°$ C. to $100°$ C., preferably about $20°$ to $50°$ C., under the hydrogen pressure of 1 to 10 atmospheres, preferably 1 to 5 atmospheres, if necessary in the presence of an acid. The acid includes mineral acids (e.g. hydrochloric acid, nitric acid, phosphoric acid, hydrobromic acid) or organic acids (e.g. acetic acid, propionic acid, tartaric acid, benzoic acid, methanesulfonic acid, toluenesulfonic acid).

Compounds of formula (Ih)

Compounds of formula (Ih)

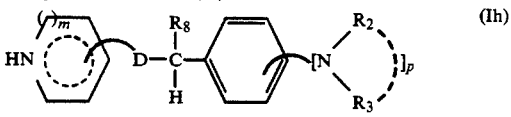

wherein D, $R_2$, $R_3$, $R_8$, m and p are respectively as defined hereinbefore can each be produced by treating a compound of formula (Ig) with an acid or a base. Thus, compound (Ie) is treated with an aqueous solution of mineral acid (e.g. nitric acid, hydrochloric acid, hydrobromic acid, iodic acid, sulfuric acid) or an alkali metal hydroxide (e.g. sodium hydroxide, potassium hydroxide, barium hydroxide, lithium hydroxide) at a temperature of generally $10°$ to $150°$ C. and preferably $50°$ to $100°$ C. The strength of the acid or base may be 1 to 10N and preferably 4 to 10N. The acid or the base is used in a proportion of about 20 to 40 equivalents relative to compound (Ig). Though it depends on reaction temperature, the reaction time is about 1 to 24 hours and preferably about 2 to 10 hours.

Compounds of formula (Ii)

Compounds of formula (Ii)

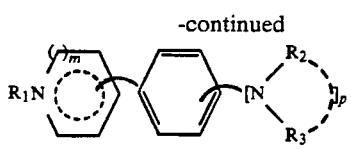

wherein $R_1$, $R_2$, $R_3$, p and m are respectively as defined hereinbefore can be produced by reacting, for example, a compound of formula (VII)

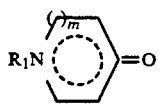

wherein $R_1$ and m are as defined above with, for example, a compound of formula (VIII)

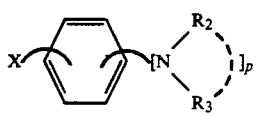

wherein $R_2$, $R_3$, p and X are respectively as defined hereinbefore and subjecting the reaction product to dehydration reaction.

The reaction between compounds (VII) and (VIII) can be conducted in an aprotic solvent, such as ethyl ether, tetrahydrofuran, dioxane or the like, using an alkyllithium (e.g. n-butyllithium, isobutyllithium, etc.) at a temperature of generally about −78° C. to 20° C. and preferably about −78° to −50° C. Generally, about 1 to 4 moles, preferably 1 to 1.5 moles, of compound (VII) is used to each mole of compound (VIII).

The dehydration reaction can be conducted in a solvent selected from among the common solvents which do not interfere with the reaction, such as aromatic solvents, e.g. benzene, toluene, xylene, etc. and ether solvents, e.g. tetrahydrofuran, dioxane, etc., if necessary in the presence of an acid catalyst such as toluenesulfonic acid, concentrated sulfuric acid, etc. at an elevated temperature of 50° to 150° C. This reaction may also be conducted by heating the material compound in a mineral acid (e.g. nitric acid, hydrochloric acid, hydrobromic acid, sulfuric acid) at 50° to 110° C.

Compounds of formula (Ij)

Compounds of formula (Ij)

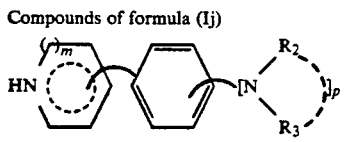

wherein $R_2$, $R_3$, p and m are respectively as defined hereinbefore can be produced by treating a compound of formula (Ii) with an acid or a base or reducing the same compound (Ii) by a per se known method. The acid or base which is used in the above treatment of compound (Ii) includes, among others, mineral acids (e.g. nitric acid, hydrochloric acid, hydrobromic acid, iodic acid, sulfuric acid, etc.) or alkali metal hydroxides (e.g. sodium hydroxide, potassium hydroxide, barium hydroxide, lithium hydroxide, etc.). This treatment can be carried out in an aqueous solution of such acid or base at a temperature of 10° to 150° C., preferably 50° to 100°. The strength of said acid or base may be about 1 to 10N and is preferably about 4 to 10N. Based on compound (Ij), the acid or the base is used generally in a proportion of about 20 to 40 equivalents. Though it depends on reaction temperature, the reaction time is generally about 1 to 24 hours and preferably about 2 to 10 hours.

Regarding the per se conventional method for reducing compound (Ij), the solvent may be any of the common solvents for organic reactions, such as water, methanol, ethanol, dimethylformamide, tetrahydrofuran, dioxane, etc., and the reaction can be conducted in such a solvent in the presence of a palladium, rhodium, platinum, Raney nickel or other catalyst at a temperature of about −10° to 100° C., preferably about 20° to 50° C., under the hydrogen pressure of 1 to 100 atmospheres, preferably 1 to 5 atmospheres, if necessary in the presence of an acid. The acid mentioned just above may be a mineral acid (e.g. hydrochloric acid, nitric acid, phosphoric acid, hydrobromic acid) or an organic acid (e.g. acetic acid, propionic acid, tartaric acid, benzoic acid, methanesulfonic acid, toluenesulfonic acid).

Compounds of formula (Ik)

Compounds of formula (Ik)

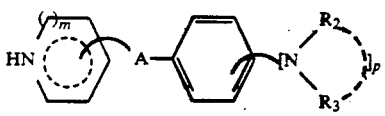

wherein A, $R_2$, $R_3$, p and m are respectively as defined hereinbefore can each be produced by subjecting a compound of formula (Ic) or (Id) to a dehydration reaction.

This dehydration reaction can be conducted in any of the common solvents which do not interfere with the reaction, such as aromatic solvents. e.g. benzene, toluene, xylene, etc. and ether solvents, e.g. tetrahydrofuran, dioxane, etc., at an elevated temperature of 50° to 150° C., if necessary in the presence of an acid catalyst such as toluenesulfonic acid, concentrated sulfuric acid and so on. The reaction can also be carried out by heating the mixture at 50° to 110° C. in a mineral acid (e.g. sulfuric acid, hydrochloric acid, hydrobromic acid, sulfuric acid, etc.).

Compounds of formula (Il)

Compounds of formula (Il)

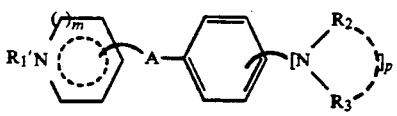

wherein $R_1'$ has the same meaning as the above definition of $R_1$ excepting a hydrogen atom, that is to say a hydrocarbon residue which may be substituted or an acyl group which may be substituted, and $R_2$, $R_3$, A, m and p are respectively as defined hereinbefore can each be produced by reacting a compound of the formula (Ib), (Id), (Ie), (Ih), (Ij) or (Ik) with a compound of formula (IX)

$R_1'X$        (IX)

wherein $R_1'$ and X are as defiend above.

The reaction of compound (Ib), (Id), (Ie), (Ih), (Ij) or (Ik) with compound (IX) can be conducted in any of the common solvents for chemical reactions, i.e. a protic solvent (e.g. water, methanol, ethanol, propanol, etc.) or an aprotic solvent (e.g. ethyl ether, tetrahydrofuran, dioxane, dimethylformamide, acetonitrile) at a temperature of generally $-10°$ to $200°$ C. and preferably $20°$ to $100°$ C.

If necessary, this reaction can be conducted in the presence of an organic base, such as pyridine, 4-dimethylaminopyridine, triethylamine, triethylenediamine, tetramethylethylenediamine, etc., an inorganic base, such as sodium hydrogen carbonate, potassium hydrogen carbonate, sodium carbonate, potassium carbonate, sodium hydroxide, potassium hydroxide, etc., or a metal hydride, such as sodium hydride, potassium hydride and so on. Based on each mole of compound (Ib), (Id), (Ie), (Ih), (Ij) or (Ik), the compound of formula (IX) is used in a proportion of generally about 1 to 10 moles and preferably about 1 to 2 moles. The reaction time is generally about 1 to 48 hours and preferably about 1 to 10 hours.

Therefore, particularly, among the compounds (I), Compounds (I') can be produced by 1) reacting a compound of the formula $$R_7'-N \text{(piperidine)}-(CH_2)_l-\overset{O}{\underset{\|}{C}}-\text{(phenyl)}-Y \quad (IV')$$

wherein M is as defined above, $R_7'$ is an acyl and Y is a halogen which can be obtained by reacting a compound of the formula $$R_7'-N \text{(piperidine)}-(CH_2)_l-\overset{O}{\underset{\|}{C}}-X$$

wherein $R_7'$ and M are of the same meaning as defined above and X is a halogen with a compound of the formula $$\text{(phenyl)}-Y \quad (III')$$

wherein Y is of the same meaning as defined above, with a compound of the formula $$HN\underset{R_3'}{\overset{R_2'}{\diagup}} \quad (V)$$

wherein $R_2$ and $R_3$ are as defined above to obtain a compound of the formula $$R_7'-N\text{(piperidine)}-(CH_2)_l-\overset{O}{\underset{\|}{C}}-\text{(phenyl)}-N\underset{R_3'}{\overset{R_2'}{\diagup}} \quad (Ia')$$

wherein all the symbols are as defined above.

2) treating a compound of the formula (Ia') as defined above with a acid or a base to obtain a compound of the formula $$HN\text{(piperidine)}-(CH_2)_l-\overset{O}{\underset{\|}{C}}-\text{(phenyl)}-N\underset{R_3'}{\overset{R_2'}{\diagup}} \quad (Ib')$$

wherein all the symbols are as defined above 3) reducing a compound of the formula (Ia') as defined above to obtain a compound of the formula $$HN\text{(piperidine)}-(CH_2)_l-\overset{O}{\underset{\|}{C}}-\text{(phenyl)}-N\underset{R_3'}{\overset{R_2'}{\diagup}} \quad (Ib')$$

wherein all the symbols are as defined above.

4) treating a compound of the formula (Ic') as defined above with an acid or a base or reducing a compound of the formula (Ib') defined above to obtain a compound of the formula $$HN\text{(piperidine)}-(CH_2)_l-\underset{OH}{CH}-\text{(phenyl)}-N\underset{R_3'}{\overset{R_2'}{\diagup}} \quad (Id')$$

wherein all the symbols are as defined above, 5) reducing a compound of the formula (Ia') or (Ic') as defined above to obtain a compound of the formula $$R_7'N\text{(piperidine)}-(CH_2)_{l+1}-\text{(phenyl)}-N\underset{R_3'}{\overset{R_2'}{\diagup}} \quad (Ie')$$

wherein all the symbols are as defined above.

6) treating a compound of the formula (Ie') as defined above with an acid or a base to obtain a compound of the formula $$HN\text{(piperidine)}-(CH_2)_{l+1}-\text{(phenyl)}-N\underset{R_3'}{\overset{R_2'}{\diagup}} \quad (If')$$

wherein all the symbols are as defined above, 7) reacting a compound of the formula (Ib'), (Id') or (If') as defined above with a compound of the formula $$R''X \quad (IX)$$

wherein R'' and X are as defined above to obtain a compound of the formula $$R_1''N\text{(piperidine)}-(CH_2)_l-D'-\text{(phenyl)}-N\underset{R_3'}{\overset{R_2'}{\diagup}} \quad (II')$$

wherein all the symbols are as defined above.

The specific conditions for the respective reactions 1)–7) are as described hereinbefore in connection with the method of production of the compounds (Ia), (Ib), (Ic), (Id), (Ie), (If) and (Ie).

As demonstrated in the test examples as mentioned below, the cyclic amine compounds (I), particularly compounds (I'''), and salts of the present invention exhibit potent antihypoxic activity in mice and brain antiedematic activity in rats.

The clinical conditions or diseases in which the cyclic amine compound (I) and salt of the present invention may be indicated include, among others, various symptoms associated with cerebral hypoxia and ischemia, various symptoms associated with elevation of intracranial pressure due to neoplasmic or traumatic compression, and other diseases such as cerebral edema, acute symptons and sequelae of cerebral apoplexy, impaired consciousness and dementia. Therefore, the cyclic amine compound (I) and salt of the invention can be used in the prevention and treatment of these symptoms and diseases.

Thus, the present invention provides a useful therapeutic drug for acute symptoms in cerebral apoplexy or sequelae of cerebral apoplexy, particularly a therapeutic drug for cerebral edema and a brain/nerve cell protecting drug.

For use of the compound of the invention in the treatment of acute symptoms in cerebral apoplexy and disturbance of microcirculation in the brain (e.g. increase in erythrocyte deformability), or the prevention and treatment of sequelae of cerebral apoplexy, and a protection of neuronal cell death or the like, including the therapy of cerebral edema, it can be administered orally or parenterally to mammals including man in various dosage forms, e.g. tablets, granules, capsules, injections and suppositories. The dosage depends on the type of disease, condition, and other factors. However, the usual adult dosage is generally 0.1 mg–3 g daily, preferably 0.3–300 mg daily, and most desirably 3–50 mg daily for administration by injection, or preferably 1 mg–1 g and most desirably 10–300 mg for oral administration.

Some of the compounds, for example compounds (I'') and their salts of the invention act on the central nervous system of mammals, where they exert potent anticholinesterase activity to show an excellent antiamnesic action against various types of induced amnesia in man and animals (e.g. mice).

Compared with physostigmine, a known cholinesterase antagonist, these compounds are characterized by a distinct separation of its action on central nerves from that on peripheral nerves, scarcely producing peripheral nervous symptoms such as spasm, salivation and diarrhea, if any, at antiamnesically effective doses and being long-acting and low in toxicity. Moreover, these compounds produce remarkable effects on oral administration.

Therefore, the compound of the invention is useful as a brain function improving agent for mammals including man.

The diseases in which the compound of the invention may be indicated are, for example, senile dementia, Alzheimer's disease, Huntington's chorea, hyperkinesia and mania. The compound can be used in the prevention or treatment of these diseases.

In employing the compound of the invention as a brain function improving agent, it can be administered orally or parenterally to mammals including man in various dosage forms, e.g. tablets, granules, capsules, injections and suppositories. Although the dosage differs according to the type of disease, condition, etc., the usual daily adult dose is about 0.001–100 mg, preferably about 0.01–30 mg, and most desirably about 0.3–10 mg.

The following working, preparation and test examples are all intended to illustrate the invention in further detail and should by no means be construed as defining the metes and bounds of the invention.

The abbreviations used in the following description have the meanings defined below:

Ac: acetyl, Bz: benzoyl, Bzl: benzyl, Cbz: benzyloxycarbonyl, $\phi$/: phenyl

The term 'room temperature' means about 10° to 30° C.

EXAMPLE 1

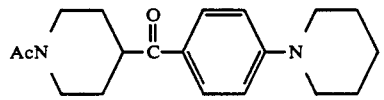

1-Acetyl-4-(4-piperidinobenzoyl)piperidine

A mixture consisting of 3.73 g of 1-acetyl-4-(4-fluorobenzoyl)piperidine and 3.0 ml of piperidine was stirred at 100° C. for 24 hours and the reaction mixture was then dissolved in 100 ml of ethyl acetate. The solution was washed with a saturated aqueous solution of sodium hydrogen carbonate and water in that order and the organic layer was dried over anhydrous magnesium sulfate. The solvent was then removed and the residue was recrystallized from ethyl acetatehexane to give 3.7 g of the title compound as colorless crystals melting at 122°–125° C.

Elemental analysis $C_{19}H_{26}N_2O_2$:
Calcd.: C, 72.58; H, 8.34; N, 8.91.
Found: C, 72.61; N, 8.28; N, 8.73.

EXAMPLE 2

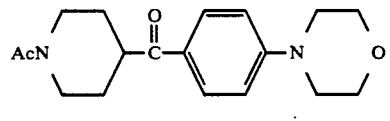

1-Acetyl-4-(4-morpholinobenzoyl)piperidine

A mixture consisting of 3.73 g of 1-acetyl-4-(4-fluorobenzoyl)piperidine and 2.6 ml of morpholine was stirred at 100° C. for 24 hours and the reaction mixture was then dissolved in 100 ml of ethyl acetate. The solution was washed with a saturated aqueous solution of sodium hydrogen carbonate and water in that order and the organic layer was dried over anhydrous magnesium sulfate. The solvent was then removed and the residual oil was purified by silica gel column chromatography (eluent: methanol:dichloromethane=1:19, v/v) to give 2.4 g of the title compound as oil.

Elemental analysis $C_{18}H_{24}N_2O_3$:
Calcd.: C, 68.33; H, 7.65; N, 8.85.
Found: C, 68.49; H, 7.54; N, 8.53.

EXAMPLE 3

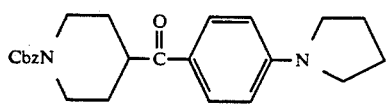

1-Carbobenzoxy-4-(4-pyrrolidinobenzoyl)piperidine

A mixture consisting of 4.1 g of 1-carbobenzoxy-4-(4-fluorobenzoyl)piperidine and 8 ml of pyrrolidine was stirred at 100° C. for 24 hours and the reaction mixtures was then worked up in the same manner as Example 2 to give 3.2 g of the title compound as oil.

Elemental analysis $C_{24}H_{28}N_2O_3$:
Calcd.: C, 73 44; H, 7.20; N, 7.14.
Found: C, 73.19; H, 7.16; N, 7.23.

EXAMPLE 4

The compounds shown in Table 1 were synthesized in substantially the same manner as Example 2 or 3.

TABLE 1

| Compound No. | Reaction process | $R_1$ | $R_8$ | Appearance | Molecular formula | Elemental analysis Calcd. (Found) C | H | N |
|---|---|---|---|---|---|---|---|---|
| 1 | 2 | Ac | N-piperidine-Bzl | oil | $C_{28}H_{32}N_2O_2$ | 77.19 (77.32 | 7.97 7.96 | 6.92 6.94) |
| 2 | 2 | Ac | N-piperazine-Bzl | " | $C_{25}H_{31}N_3O_2$ | 74.04 (74.15 | 7.71 7.73 | 10.36 10.15) |
| 3 | 2 | Ac | N(CH₃)(CH₂φ) | " | $C_{22}H_{26}N_2O_2$ | 75.40 (75.35 | 7.48 7.25 | 7.99 7.78) |
| 4 | 2 | Ac | N(CH₃)₂ | 132–133° C. (mp) | $C_{16}H_{22}N_2O_2$ | 70.05 (70.13 | 8.08 7.94 | 10.2 10.31) |
| 5 | 3 | Cbz | piperidino | Oil | $C_{25}H_{30}N_2O_3$ | 73.86 (73.95 | 7.44 7.17 | 6.89 6.86) |
| 6 | 3 | Cbz | hexamethyleneimino | " | $C_{26}H_{32}N_2O_3$ | 74.26 (74.27 | 7.67 7.37 | 6.66 6.52) |
| 7 | 2 | Ac | N(Et)₂ | 111–113° C. (mp) | $C_{18}H_{26}N_2O_2$ | 71.49 (71.46 | 8.67 8.49 | 9.26 9.13) |
| 8 | 2 | Ac | N((CH₂)₂CH₃)₂ | Oil | $C_{20}H_{30}N_2O_2$ | 72.69 (72.72 | 9.15 9.10 | 8.48 8.57) |
| 9 | 2 | Ac | H, NCH₃ | Oil | $C_{15}H_{20}N_2O_2$ | 69.20 (69.28 | 7.74 7.51 | 10.76 10.65) |
| 10 | 2 | Ac | H, NCH₂φ | Oil | $C_{21}H_{24}N_2O_2$ | 74.97 (74.63 | 7.19 7.02 | 8.33 8.17) |
| 11 | 2 | Ac | H, NCH₂CH₃ | Oil | $C_{16}H_{22}N_2O_2$ | 70.04 (69.90 | 8.08 8.14 | 10.17 10.21) |

TABLE 1-continued

[Structure: R₁-N(piperidine)-C(=O)-phenyl-R₈]

| Compound No. | Reaction process | R₁ | R₈ | Appearance | Molecular formula | Elemental analysis Calcd. (Found) | | |
|---|---|---|---|---|---|---|---|---|
| | | | | | | C | H | N |
| 12 | 2 | Ac | (pyrrolidine N) | Oil | $C_{18}H_{24}N_2O_2$ | 71.97 (71.86) | 8.05 (8.06) | 9.33 (9.49) |
| 13 | 2 | Ac | (azepane N) | Oil | $C_{20}H_{28}N_2O_2$ | 73.14 (73.05) | 8.59 (8.30) | 8.53 (8.33) |

EXAMPLE 5

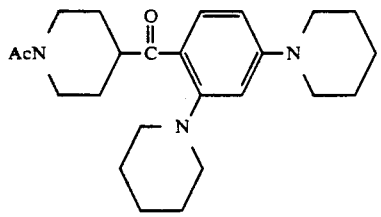

1-Acetyl-4-[2,4-di(piperidino)benzoyl]piperidine

A mixture consisting of 2.67 g of 1-acetyl-4-(2,4-difluorobenzoyl)piperidine and 5.0 ml of piperidine was stirred at 100° C. for 24 hours and the reaction mixture was then worked up in the same manner as Example 2 to give 3.3 g of the title compound as oil.

Elemental analysis $C_{24}H_{35}N_3O_2$:
Calcd.: C, 72.51; H, 8.87; N, 10.57.
Found: C, 72.32; H, 8.63; N, 10.58.

EXAMPLE 6

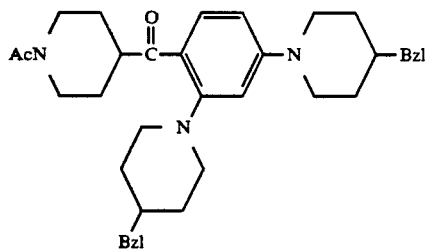

1-Acetyl-4-[2,4-di[(4-benzyl)piperidino]benzoyl]piperidine

A mixture consisting of 2.67 g of 1-acetyl-4-(2,4-difluorobenzoyl)piperidine and 8.8 ml of 4-benzylpiperidine was stirred at 100° C. for 24 hours and the reaction mixture was then worked up in the same manner as Example 2 to give 4.1 g of the title compound as oil.

Elemental analysis $C_{38}H_{47}N_3O_2$:
Calcd.: C, 78.99; H, 8.20; N, 7.27.
Found: C, 79.10; H, 8.39; N, 7.15.

EXAMPLE 7

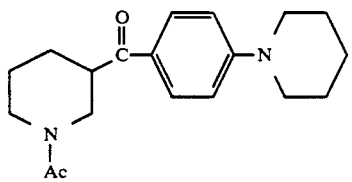

1-Acetyl-3-(4-piperidinobenzoyl)piperidine

A mixture consisting of 3.73 g of 1-acetyl-3-(4-fluorobenzoyl)piperidine and 5 ml of piperidine was stirred at 100° C. for 24 hours and the reaction mixture was then worked up in the same manner as Example 1. The residue was recrystallized from ethyl ether-n-hexane to give 3.2 g of colorless crystals melting at 116°-120° C.

Elemental analysis $C_{19}H_{28}N_2O_2$:
Calcd.: C, 72.58; H, 8.34; N, 8.91.
Found: C, 72.52; N, 8.06; N, 8.73.

EXAMPLE 8

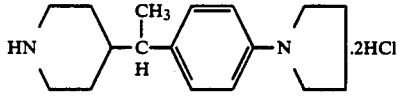

4-(α-Methyl-4-pyrrolidinobenzyl)piperidine dihydrochloride

To magnesium metal (2 g) was added dry ethyl ether (30 ml) followed by addition of iodomethane until the magnesium metal was consumed. To this solution was added 1.96 g of the 1-carbobenzoxy-4-(4-pyrrolidinobenzoyl)piperidine prepared in Example 3 and the mixture was refluxed for 2 hours. To this reaction mixture was added an aqueous solution of ammonium chloride and the precipitate was filtered off. The filtrate was extracted with dichloromethane and the solvent was then distilled off. The residue was purified by silica gel column chromatography (eluent: methanol:dichloromethane=1:100, v/v) and the resulting oil (0.7 g) was dissolved in a mixture of methanol (50 ml) and 1N-methanolic hydrochloric acid (2 ml), followed by addition of 10% palladium-on-carbon. The catalytic reduction was carried out in a hydrogen stream at atmospheric temperature and pressure for 20 hours. After completion of the reaction, the catalyst was removed and the solvent was distilled off to give 0.5 g of the title compound as a colorless amorphous soild.

Elemental analysis $C_{17}H_{28}Cl_2N_2$:
Calcd: C, 61.62; H, 8.52; N, 8.45.
Found: C, 61.39; H, 8.37; N, 8.48.

EXAMPLE 9

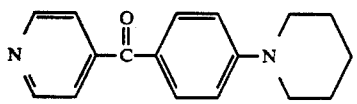

4-(4-Piperidinobenzoyl)pyridine

A mixture consisting of 4.76 g of 4-(4-fluorobenzoyl)pyridine and 9.8 ml of piperidine was stirred at 100° C. for 24 hours and the reaction mixture was then worked up in the same manner as Example 3 to give 5.3 g of the title compound as a yellow oil.

Elemental analysis $C_{17}H_{18}N_2O$:
Calcd: C, 76.66; H, 6.81; N, 10.52.
Found: C, 76.70; H, 6.79; N, 10.56.

EXAMPLE 10

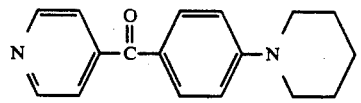

4-(4-Piperidinobenzoyl)piperidine dihydrochloride

The 1-acetyl-4-(4-piperidinobenzoyl)piperidine (0.63 g) prepared in Example 1 was dissolved in 10 ml of concentrated hydrochloric acid and the solution was stirred at 100° C. for 3 hours. The solvent was then distilled off under reduced pressure and the residue was recrystallized from ethanol to give 0.5 g of colorless crystals melting at 256°-264° C.

Elemental analysis $C_{17}H_{26}Cl_2N_2O$:
Calcd: C, 59.13; H, 7.59; N, 8.11.
Found: C, 58.92; H, 7.44; N, 8.31.

EXAMPLE 11

The compounds shown in Table 2 were synthesized in substantially the same manner as Example 10.

TABLE 2

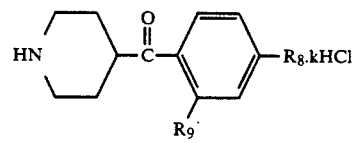

| Compound No. | $R_8$ | $R_9$ | k | Melting point (°C.) | Molecular formula | Elemental analysis Calcd. (Found) | | |
|---|---|---|---|---|---|---|---|---|
| | | | | | | C | H | N |
| 1 | pyrrolidinyl (N-ring) | H | 2 | 255-260 | $C_{16}H_{24}Cl_2N_2O$ | 58.01 (57.94 | 7.30 7.18 | 8.46 8.49) |
| 2 | azepanyl (N-ring) | H | 2 | 142-145 | $C_{18}H_{28}Cl_2N_2O$ | 60.16 (60.04 | 7.85 7.86 | 7.80 7.85) |
| 3 | N-Bzl piperidinyl | H | 2 | 239-241 | $C_{24}H_{32}Cl_2N_2O$ | 66.20 (66.35 | 7.41 7.29 | 6.43 6.47) |
| 4 | N-Bzl piperazinyl | H | 3 | 205-207 | $C_{23}H_{32}Cl_3N_3O$ | 58.41 (58.71 | 6.82 6.56 | 8.89 8.75) |
| 5 | N(CH$_3$)$_2$ | H | 2 | 252-257 | $C_{14}H_{22}Cl_2N_2O$ | 55.08 (55.14 | 7.26 7.15 | 9.18 9.23) |

TABLE 2-continued

| Compound No. | R8 | R9 | k | Melting point (°C.) | Molecular formula | Elemental analysis Calcd. (Found) | | |
|---|---|---|---|---|---|---|---|---|
| | | | | | | C | H | N |
| 6 | (piperidino) | (piperidino) | 3 | 196-204 | $C_{22}H_{36}Cl_3N_3O$ | 56.83 (56.75 | 7.81 7.60 | 9.04 9.23) |
| 7 | (N-Bzl piperidino) | (N-Bzl piperidino) | 3 | Amorphous solid | $C_{38}H_{48}Cl_3N_3O$ | 67.02 (66.90 | 7.50 7.36 | 6.51 6.30) |

EXAMPLE 12

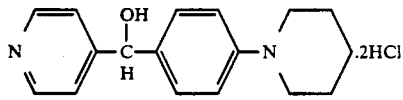

4-[(α-Hydroxy-4-piperidino)benzyl]pyridine dihydrochloride

In 30 ml of ethanol was dissolved 2.66 g of the 4-(4-piperidinobenzoyl)pyridine prepared in Example 9, followed by addition of 1.0 ml of concentrated hydrochloric acid. Using 10% palladium-on-carbon as the catalyst, catalytic reduction was carried out at atmospheric temperature and pressure for 5 hours. After completion of the reaction, the catalyst and the solvent were successively removed and the residue was recrystallized from ethanol-ethyl acetate to give 1.3 g of colorless crystals melting at 151°-154° C.

Elemental analysis $C_{17}H_{22}Cl_2N_2O$:
Calcd.: C, 59.83; H, 6.50; N, 8.21.
Found: C, 59.70; H, 6.39; N, 8.14.

EXAMPLE 13

4-[(α-Hydroxy-4-piperidino)benzyl]piperidine dihydrochloride

In a solvent mixture of ethanol (10 ml) and water (1 ml) was dissolved 1.04 g of the 4-(4-piperidinobenzoyl)-piperidine dihydrochloride prepared in Example 10, followed by dropwise addition of 0.44 g of sodium borohydride at room temperature. The mixture was stirred for 4 hours at room temperature and the insolubles were filtered off. The solvent was then removed and the residue was dissolved in dichloromethane (50 ml). After the insolubles were filtered off, 2 ml of 4N-methanolic hydrochloric acid was added and the solvent was distilled off. The residue was recrystallized from ethanol to give 1.4 g of colorless crystals melting at 205°-217° C.

EXAMPLE 14

The compounds shown in Table 3 were prepared in substantially the same manner as Example 13.

TABLE 3

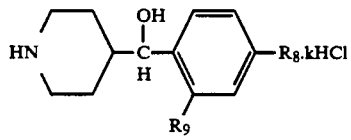

| Compound No. | R8 | R9 | k | Melting point (°C.) | Molecular formula | Elemental analysis Calcd. (Found) | | |
|---|---|---|---|---|---|---|---|---|
| | | | | | | C | H | N |
| 1 |  | H | 2 | 144-148 | $C_{16}H_{26}Cl_2N_2O$ | 57.66 (57.51 | 7.87 7.67 | 8.40 8.49) |

TABLE 3-continued

[Structure: HN-piperidine-CH(OH)-phenyl(R9)-R8·kHCl]

| Compound No. | R8 | R9 | k | Melting point (°C.) | Molecular formula | Elemental analysis Calcd. (Found) | | |
|---|---|---|---|---|---|---|---|---|
| | | | | | | C | H | N |
| 2 | azepane (N) | H | 2 | Amorphous solid | $C_{18}H_{30}Cl_2N_2O$ | 59.83 (59.83 | 8.37 8.25 | 7.75 7.93) |
| 3 | N-piperidine-Bzl | H | 2 | 174–175 | $C_{24}H_{34}Cl_2N_2O$ | 65.89 (65.94 | 7.83 7.79 | 6.40 6.49) |
| 4 | N-piperazine-N-Bzl | H | 3 | 157–159 | $C_{23}H_{34}Cl_3N_3O$ | 58.17 (58.20 | 7.22 7.09 | 8.85 8.59) |
| 5 | N(CH3)2 | H | 2 | 159–161 | $C_{14}H_{24}Cl_2N_2O$ | 54.72 (54.70 | 7.87 7.98 | 9.12 9.19) |
| 6 | N-piperidine | N-piperidine | 3 | Amorphous solid | $C_{22}H_{38}Cl_3N_3O$ | 56.59 (56.31 | 8.20 8.15 | 9.00 9.16) |
| 7 | N-piperidine-Bzl | N-piperidine-Bzl | 3 | Amorphous solid | $C_{36}H_{50}Cl_3N_3O$ | 66.81 (66.63 | 7.79 7.75 | 6.49 6.67) |

EXAMPLE 15

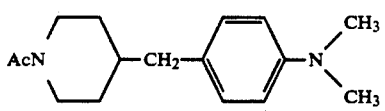

1-Acetyl-4-(4-dimethylaminobenzyl)piperidine

In 100 ml of ethanol was dissolved 5.49 g of the 1-acetyl-4-(4-dimethylaminobenzoyl)piperidine (Compound No. 4) prepared in Example 4, followed by addition of concentrated hydrochloric acid (2 ml). Using 10% palladium-on-carbon as the catalyst, catalytic reduction was carried out at atmospheric temperature and pressure for 48 hours. After completion of the reaction, the solvent was distilled off and the residual oil was dissolved in ethyl acetate (100 ml). The solution was washed with a saturated aqueous solution of sodium hydrogen carbonate and water in that order and dried over anhydrous magnesium sulfate. The solvent was then distilled off and the residual oil was subjected to silica gel column chromatography (eluent: methanol:dichloromethane=1:19, v/v) to give 3.9 g of the title compound as a colorless oil.

Elemental analysis $C_{16}H_{24}N_2O$:
Calcd: C, 73.81; H, 9.29; N, 10.76.
Found: C, 73.57; H, 9.36; N, 10.90.

EXAMPLE 16

The compounds shown in Table 4 were prepared in substantially the same manner as Example 15.

TABLE 4

$$AcN\text{-piperidine-}CH_2\text{-}C_6H_3(R_9)\text{-}R_8 \cdot kHCl$$

| Compound No. | $R_8$ | $R_9$ | k | Appearance | Molecular formula | Elemental analysis Calcd. (Found) C | H | N |
|---|---|---|---|---|---|---|---|---|
| 1 | piperidino | H | 1 | Amorphous solid | $C_{19}H_{29}ClN_2O$ | 67.74 (67.80) | 8.68 (8.57) | 8.31 (8.16) |
| 2 | 4-Bzl-piperidino | H | 1 | Amorphous solid | $C_{26}H_{35}ClN_2O$ | 73.13 (73.25) | 8.26 (8.20) | 6.5 (6.76) |
| 3 | piperidino | piperidino | 2 | Amorphous solid | $C_{24}H_{39}Cl_2N_3O$ | 63.14 (63.18) | 8.61 (8.47) | 9.20 (9.18) |
| 4 | morpholino | H | 1 | Amorphous solid | $C_{18}H_{27}ClN_2O_2$ | 63.80 (63.82) | 8.03 (8.19) | 8.27 (8.32) |
| 5 | $N(Et)_2$ | H | 0 | Oil | $C_{18}H_{28}N_2O$ | 74.96 (74.87) | 9.79 (9.65) | 9.71 (9.57) |
| 6 | $N((CH_2)_2CH_3)_2$ | H | 0 | Oil | $C_{20}H_{32}N_2O$ | 75.90 (75.73) | 10.19 (10.18) | 8.85 (8.53) |
| 7 | $NHCH_3$ | H | 0 | Oil | $C_{15}H_{22}N_2O$ | 73.13 (73.39) | 9.00 (8.97) | 11.37 (11.45) |
| 8 | $NHCH_2CH_3$ | H | 0 | Oil | $C_{16}H_{24}N_2O$ | 73.81 (73.66) | 9.29 (9.10) | 10.76 (10.47) |

EXAMPLE 17

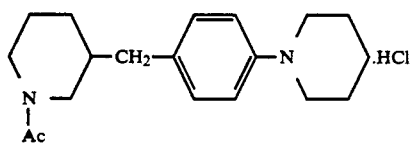

1-Acetyl-3-(4-piperidinobenzyl)piperidine monohydrochloride

The 1-acetyl-3-(4-piperidinobenzoyl)piperidine prepared in Example 7 was treated in the same manner as Example 15 to give the desired compound, which was converted to the hydrochloride. The procedure gave 1.1 g of a colorless amorphous solid.

Elemental analysis $C_{19}H_{29}ClN_2O$:
Calcd.: C, 67.74; H, 8.68; N, 8.31.
Found C, 67.91; H, 8.73; N, 8.28.

EXAMPLE 18

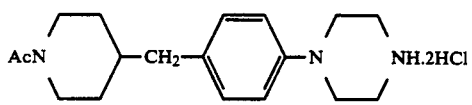

1-Acetyl-4-(4-piperazinobenzyl)piperidine dihydrochloride

In 100 ml of ethanol was dissolved 4.8 g of the 1-acetyl-4-(4-piperazinobenzoyl)piperidine (Compound No. 2) prepared in Example 4, followed by addition of 3.5 ml of concentrated hydrochloric acid. The reaction mixture was worked up in the same manner as Examples 15 and 17 to give a solid, which was recrystallized from ethanol-ethyl acetate. The procedure gave 3.0 g of a hygroscopic colorless solid melting at 136°-137° C.

Elemental analysis $C_{18}H_{29}Cl_2N_3O$:
Calcd.: C, 57.75; H, 7.81; N, 11.22.
Found: C, 57.51; H, 7.60; N, 11.37.

EXAMPLE 19

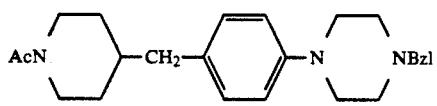

1-Acetyl-4-(4-benzylpiperazinobenzyl)piperidine

In 20 ml of ethanol was dissolved 1.16 g of the 1-acetyl-4-(4-piperazinobenzyl)piperidine dihydrochloride prepared in Example 18, followed by addition of 1.38 g of potassium carbonate and 0.4 ml of benzyl bromide. The mixture was refluxed for 20 hours and the insolubles were filtered off. The solvent was then distilled off and the oil was isolated and purified by silica gel column chromatography (eluent: methanol: dichloromethane=1:19, v/v) to give 0.85 g of the title compound as a colorless oil.

Elemental analysis $C_{25}H_{33}N_3O$:
Calcd: C, 76.69; H, 8.50; N, 10.73.
Found: C, 76.82; H, 8.59; N, 10.59.

EXAMPLE 20

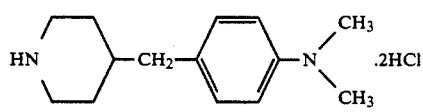

4-(4-Dimethylaminobenzyl)piperidine dihydrochloride

In 30 ml of concentrated hydrochroic acid was dissolved 3.5 g of the 1-acetyl-4-(4-dimethylaminobenzyl)-piperidine prepared in Example 15 and the solution was stirred at 100° C. for 20 hours. The solvent was then distilled off and the residual oil was subjected to silica gel column chromatography (eluent: n-butanol: acetic acid:ethyl acetate:water=1:1:1:1, v,v) to give 3.1 g of the title compound as an amorphous solid.

Elemental analysis $C_{14}H_{24}Cl_2N_2$:
Calcd: C, 57.73; H, 8.31; N, 9.62.
Found: C, 57.49; H, 8.24; N, 9.68.

EXAMPLE 21

The compounds shown in Table 5 were prepared in substantially the same manner as Example 20.

TABLE 5

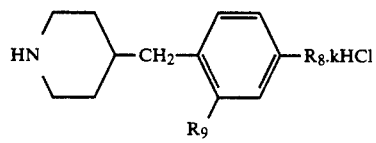

| Compound No. | $R_8$ | $R_9$ | k | Melting point (°C.) | Molecular formula | Elemental analysis Calcd. (Found) C | H | N |
|---|---|---|---|---|---|---|---|---|
| 1 | ⟨N-piperidine⟩ | H | 2 | 148–152 | $C_{17}H_{28}Cl_2N_2$ | 61.62 (61.68 | 8.52 8.58 | 8.45 8.39) |
| 2 | N⟨⟩-Bzl | H | 2 | Amorphous solid | $C_{24}H_{34}Cl_2N_2$ | 68.39 (68.30 | 8.13 8.14 | 6.65 6.70) |
| 3 | ⟨N⟩ | ⟨N⟩ | 3 | Amorphous solid | $C_{22}H_{38}Cl_3N_3$ | 58.60 (58.39 | 8.49 8.66 | 9.32 9.45) |
| 4 | N⟨⟩NH | H | 3 | 108–109 | $C_{16}H_{28}Cl_3N_3$ | 52.11 (52.10 | 7.65 7.42 | 11.39 11.46) |
| 5 | N⟨⟩N—Bzl | H | 3 | 150–154 | $C_{23}H_{34}Cl_3N_3$ | 60.20 (60.37 | 7.47 7.25 | 9.16 9.22) |
| 6 | N⟨⟩O | H | 2 | Amorphous solid | $C_{16}H_{26}Cl_2N_2O$ | 57.66 (57.56 | 7.86 7.83 | 8.40 8.25) |

TABLE 5-continued

[Structure: HN-piperidine-CH2-phenyl(R9)-R8·kHCl]

| Compound No. | R8 | R9 | k | Melting point (°C.) | Molecular formula | Calcd. (Found) C | H | N |
|---|---|---|---|---|---|---|---|---|
| 7 | N(Et)(Et) | H | 2 | 158-161 | C16H28Cl2N2 | 60.19 (60.12 | 8.84 8.82 | 8.77 8.49) |
| 8 | N(Me)(H) | H | 2 | 152-157 | C13H22Cl2N2 | 56.32 (56.46 | 8.00 8.05 | 10.10 10.17) |
| 9 | N((CH2)2CH3)2 | H | Fumaric acid | 104-105 | C22H34N2O4 | 67.66 (67.87 | 8.78 8.73 | 7.17 6.92) |
| 10 | N(Et)(H) | H | 2/Fumaric acid | 85-88 | C22H30N2O8 | 58.66 (58.41 | 6.71 6.63 | 6.22 6.31) |
| 11 | N-pyrrolidinyl | H | 2/Fumaric acid | 173-175 | C24H32N2O8 | 60.49 (60.20 | 6.77 6.47 | 5.88 5.87) |

EXAMPLE 22

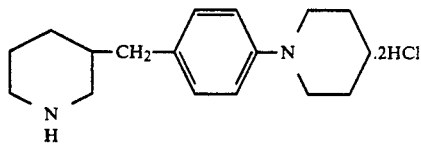

3-(4-Piperidinobenzyl)piperidine dihydrochloride

The 1-acetyl-3-(4-piperidinobenzyl)piperidine monohydrochloride (1.40 g) prepareed in Example 17 was treated in the same manner as Example 20 to give 0.8 g of a colorless amorphous solid.

Elemental analysis C17H28Cl2N2:
Calcd.: C, 61.62; H, 8.52; N, 8.45.
Found: C, 61.40; H, 8.31; N, 8.60.

EXAMPLE 23

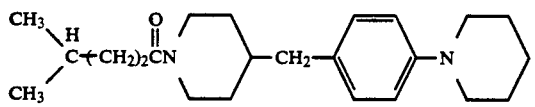

1-(4-Methyl)pentanoyl-4-(4-piperidinobenzyl)piperidine

In 10 ml of dimethylformamide was dissolved 0.85 g of the 4-(4-piperidinobenzyl)piperidine dihydrochloride (Compound No. 1) prepared in Example 21, followed by addition of 1.02 ml of triethylamine, 0.42 g of isocaproic acid and 0.6 g of diethyl cyanophosphate. The mixture was stirred for 2 hours at room temperature and the solvent was distilled off. The residual oil was purified by silica gel column chromatography (eluent: methanol:dichloromethane=1:19, v/v) to give 0.8 g of the title compound as a colorless oil.

Elemental analysis C23H36N2O:
Calcd.: C, 77.48; H, 10.18; N, 7.86.
Found: C, 77.57; H, 10.13; N, 7.96.

EXAMPLE 24

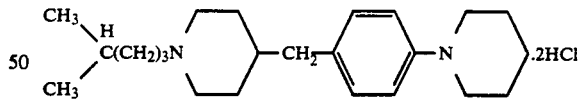

1-(4-Methyl)pentyl-4-(4-piperidinobenzyl)piperidine dihydrochloride

In 30 ml of tetrahydrofuran was dissolved 0.7 g of the 1-(4-methyl)pentanoyl-4-(4-piperidinobenzyl)piperidine prepared in Example 23, followed by addition of 0.23 g of lithium aluminium hydride. The mixture was heated under reflux for 10 minutes and, then, 0.45 ml of water and 0.33 ml of 10% aqueous sodium hydroxide solution were added. The mixture was stirred for 1 hour at room temperature and the insolubles were filtered off. To the filtrate was added 5 ml of 1N-hydrochloric acid and the solvent was distilled off. The residual solid was recrystallized from dioxane to give 0.66 g of colorless crystals melting at 174°-178° C.

Elemental analysis C23H40Cl2N2:

Calcd.: C, 66.49; H, 9.70; N, 6.72.
Found: C, 66.43; H, 9.53; N, 6.54.

EXAMPLE 25

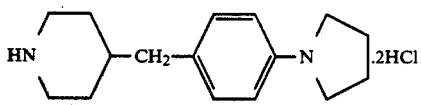

4-(4-Pyrrolidinobenzyl)piperidine dihydrochloride

In a solvent mixture of 20 ml of ethanol and 20 ml of water was added 3.33 g of the 4-(4-pyrrolidinobenzoyl)-piperidine dihydrochloride (Compound No. 1) prepared in Example 11, followed by addition of 10% palladium-on-carbon, and the catalytic reduction was carried out at atmospheric temperature and pressure for 2 hours. After completion of the reaction, the solvent was distilled off and the residue was dissolved in a saturated aqueous solution of sodium chloride. The solution was made basic by addition of solid sodium hydrogen carbonate and extracted with acetonitrile. The extract was dried over anhydrous sodium sulfate and the solvent was distilled off. After addition of 2N-methanolic hydrochloric acid to the oily residue, the solvent was distilled off and the residue was recrystallized from ethyl ether-methanol to give 0.4 g of colorless crystals melting at 152°–154° C.

Elemental analysis $C_{16}H_{26}Cl_2N_2$:
Calcd. C, 60.56; H, 8.26; N, 8.83.
Found: C, 60.40; H, 8.45; N, 8.70.

EXAMPLE 26

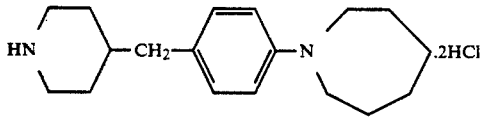

4-(4-Homopiperidinobenzyl)piperidine dihydrochloride

The 4-(4-homopiperidinobenzoyl)piperidine dihydrochloride (3.6 g, Compound No. 2) prepared in Example 11 was subjected to catalytic reduction in the same manner as Example 25 and the reaction product was purified by silica gel column chromatography (eluent: n-butanol:acetic acid:ethyl acetate:water=1:1:1:1). The fractions rich in the desired compound were pooled and the solvent was distilled off. The product compound was then converted to the hydrochloride in the same manner as Example 25. The procedure gave 0.7 g of a colorless amorphous solid.

Elemental analysis $C_{18}H_{30}Cl_2N_2$:
Calcd.: C, 62.60; H, 8.62; N, 8.11.
Found C, 62.37; H, 8.36; N, 7.92.

EXAMPLE 27

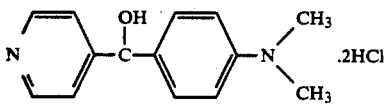

4-[(α-Hydroxy-4-dimethylamino)benzyl]pyridine dihydrochloride

1) A mixture consisting of 2.38 g of 4-(4-fluorobenzoyl)pyridine and 7 ml of 50% aqueous dimethylamine solution was stirred for 24 hours at room temperature, followed by addition of 100 ml of ethyl acetate. The mixture was washed with a saturated aqueous solution of sodium hydrogen carbonate and the organic layer was dried over anhydrous sodium sulfate. The solvent was then distilled off and the residue was recrystallized from ethanol-ethyl acetate to give 1.1 g of 4-(4-dimethylaminobenzoyl)pyridine as pale yellow crystals melting at 122°–124° C.

2) 4-(4-Dimethylaminobenzoyl)pyridine (1.0 g) was treated in the same manner as Example 12 to give 1.1 g of the title compound as pale yellow crystals melting at 133°–136° C.

Elemental analysis $C_{14}H_{18}Cl_2N_2O$:
Calcd.: C, 55.83; H, 6.01; N, 9.30.
Found: C, 55.83; H, 6.21; N, 9.07.

EXAMPLE 28

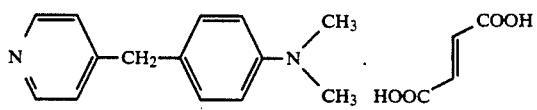

4-(4-Dimethylaminobenzyl)pyridine fumarate

In 10 ml of acetic acid was dissolved 1.25 g of the 4-[(α-hydroxy-4-dimethylamino)benzyl]pyridine dihydrochloride prepared in Example 27, followed by addition of 1.75 g of ammonium formate. Using 10% palladium-on-carbon as the catalyst, the above mixture was stirred at 110° C. in a nitrogen stream for 30 minutes. The catalyst was then filtered off and the solvent was distilled off. The remaining oil was dissolved in a saturated aqueous solution of sodium chloride, and the solution was made basic by addition of solid sodium hydrogen carbonate and extracted with acetonitrile. The solvent was then distilled off and the remaining oil was purified by silica gel column chromatography (eluent: ethyl acetate). The resulting oily compound was converted to the fumarate by the conventional procedure. The above procedure gave 1.2 g of pale yellow crystals melting at 132°–134° C.

Elemental analysis $C_{18}H_{20}N_2O_4$:
Calcd.: C, 65.84; H, 6.14; N, 8.53.
Found: C, 65.89; H, 6.19; N, 8.31.

EXAMPLE 29

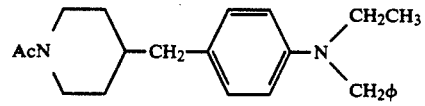

1-Acetyl-4-[4-(N-benzyl-N-ethylamino)benzyl]piperidine

In 30 ml of ethanol was dissolved 3.13 g of the 1-acetyl-4-[4-(ethylamino)benzyl]piperidine (Compound No. 8) prepared in Example 16, followed by addition of 3.31 g of potassium carbonate and 1.43 ml of benzyl bromide. The mixture was refluxed for 2 hours and the insolubles were filtered off. The solvent was then distilled off and the remaining oil was purified by silica gel column chromatography (eluent: ethyl acetate) to give 3.8 g of the title compound as a colorless oil.

Elemental analysis $C_{23}H_{30}N_2O$:
Calcd.: C, 78.81; H, 8.63; N, 7.99.
Found: C, 78.53; H, 8.68; N, 7.75.

EXAMPLE 30

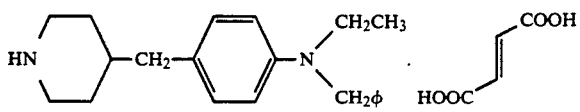

4-[4-(N-Benzyl-N-ethylamino)benzyl]piperidine fumarate

In 30 ml of concentrated hydrochloric acid was dissolved 3.5 g of the 1-acetyl-4-[4-(N-benzylethylamino)-benzyl]piperidine prepared in Example 29 and the solution was stirred at 100° C. for 24 hours. The solvent was then distilled off and the oily residue was dissolved in water and made basic by addition of solid sodium hydrogen carbonate. The solution was extracted with dichloromethane and the extract was dried over anhydrous magnesium sulfate. The solvent was then distilled off and the remaining compound was converted to the fumarate by the conventional procedure. The resulting product was recrystallized from ethanol-ethyl acetate to give 2.0 g of the title compound as colorless crystals melting at 128°-130° C.

Elemental analysis $C_{25}H_{32}N_2O_4$:
Calcd.: C, 70.73; H, 7.60; N, 6.60.
Found C, 70.96; H, 7.62; N, 6.57.

EXAMPLE 31

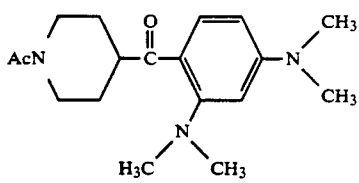

1-Acetyl-4-[2,4-bis(dimethylamino)]benzoylpiperidine

A mixture consisting of 2.67 g of 1-acetyl-4-(2,4-difluorobenzoyl)piperidine and 10 ml of 50% aqeuous dimethylamine solution was heated at 150° C. for 15 hours, followed by addition of a saturated aqueous solution of sodium hydrogen carbonate. The mixture was extracted with ethyl acetate and the extract was dried over anhydrous magnesium sulfate. The solvent was then distilled off and the oily residue was purified by silica gel column chromatogrpahy (eluent: ethyl acetate) to give 1.8 g of the title compound as a pale yellow oil.

Elemental analysis $C_{18}H_{27}N_3O_2$:
Calcd.: C, 68.11; H, 8.57; N, 13.24.
Found: C, 67.86; H, 8.51; N, 13.36.

EXAMPLE 32

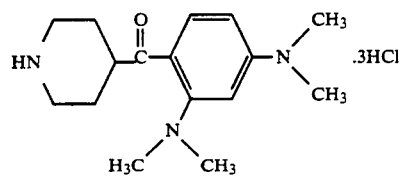

4-[2,4-bis(Dimethylamino)benzoyl]piperidine trihydrochloride

The 1-acetyl-4-[2,4-[bis(dimethylamino)]benzoyl]-piperidine (1.8 g) prepared in Example 31 was treated in the same manner as Example 10 to give 1.37 g of the title compound as colorless crystals melting at 211°-214° C.

Elemental analysis $C_{16}H_{28}Cl_3N_3O$:
Calcd.: C, 49.94; H, 7.33; N, 10.92.
Found: C, 49.80; H, 7.16; N, 10.74.

EXAMPLE 33

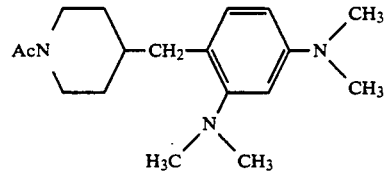

1-Acetyl-4-[2,4-bis(dimethylamino)benzyl]piperidine

The 1-acetyl-4-[2,4-[bis(dimethylamino)]benzoyl]-piperidine (6.34 g) prepared in Example 31 was treated in the same manner as Example 15 to give 2.6 g of the title compound as a colorless oil.

NMR (CDCl$_3$): δ1.0-1.5 (2H, m), 1.5-1.9 (3H, m), 2.04 (3H, s), 2.3-2.7 (1H, m), 2.53 (2H, d), 2.63 (6H, s), 2.8-3.2 (1H, m), 2.92 (6H, s), 3.6-3.9 (1H, m), 4.4-4.7 (1H, m), 6.4-6.6 (2H, m), 6.9-7.1 (1H, m)

EXAMPLE 34

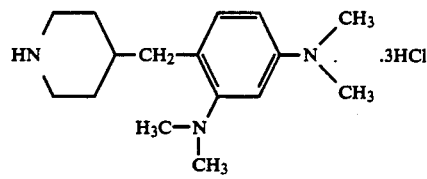

4-[2,4-bis(Dimethylamino)benzyl]piperidine trihydrochloride

The 1-acetyl-4-[2,4-[bis(dimethylamino)]benzyl]-piperidine (2.4 g) prepared in Example 33 was treated in the same manner as Example 20 to give 2.1 g of the title compound as a colorless amorphous solid.

Elemental analysis C₁₆H₃₀Cl₃N₃:
Calcd.: C, 51.83; H, 8.15; N, 11.33.
Found: C, 51.87; H, 8.10; N, 11.22.

EXAMPLE 35

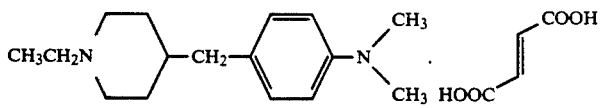

1-Ethyl-4-(4-dimethylaminobenzyl)piperidine fumarate

In 30 ml of tetrahydrofuran was dissolved 2.6 g of the 1-acetyl-4-(4-dimethylaminobenzyl)piperidine prepared in Example 15, followed by addition of 0.56 g of lithium aluminum hydride. The mixture was stirred under heating for 30 minutes and 1.1 ml of water and 0.9 ml of 10% aqueous sodium hydroxide solution were added. The mixture was stirred for 1 hour at room temperature and the insolubles were filtered off. The solvent was then distilled off under reduced pressure and the residue was diluted with dichloromethane. The insolubles were filtered off and the solvent was distilled off to give 2.53 g of an oily compound, which was converted to the fumarate by the conventional procedure. This product was recrystallized from ethanol-ethyl acetate to give 2.26 g of the title compound as colorless crystals melting at 128°–132° C.

Elemental analysis C₂₀H₃₀N₂O₄:
Calcd.: C, 66.27; H, 8.34; N, 7.73.
Found: C, 66.37; H, 8.21; N, 7.71.

EXAMPLE 36

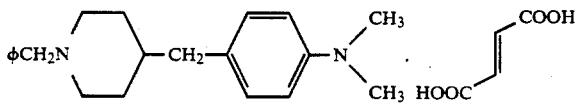

1-Benzyl-4-(4-dimethylaminobenzyl)piperidine fumarate

1-Benzoyl-4-(4-dimethylaminobenzyl)piperidine (1.3 g), which was prepared from the 4-(4-dimethylaminobenzyl)piperidine dihydrochloride of Example 20 and benzoyl chloride in the per se conventional manner, was treated in the same manner as Example 35 to give 0.45 g of the title compound as colorless crystals melting at 182°–183° C.

Elemental analysis C₂₅H₃₂N₂O₄:
Calcd.: C, 70.73; H, 7.60; N, 6.60.
Found: C, 70.79; H, 7.35; N, 6.52.

EXAMPLE 37

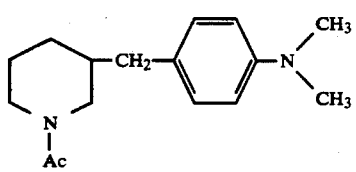

1-Acetyl-3-(4-dimethylaminobenzyl)piperidine

1) A mixture consisting of 2.49 g of 1-acetyl-3-(4-fluorobenzoyl)piperidine and 8 ml of 50% aqueous dimethylamine solution was stirred for 5 days at room temperature, followed by addition of a saturated aqueous solution of sodium hydrogen carbonate. The solution was extracted with ethyl acetate and the extract was dried. The solvent was then distilled off and the remaining oil was purified by silica gel column chromatography (eluent: ethyl acetate) to give 2.6 g of 1-acetyl-3-(4-dimethylaminobenzoyl)piperidine as a pale yellow oil.

2) 1-Acetyl-3-(4-dimethylaminobenzoyl)piperidine (2.5 g) was treated in the same manner as Example 15 to give 2.0 g of a colorless oil.

NMR (CDCl₃): δ1.0–1.4 (2H, m), 1.4–1.9 (3H, m), 2.01 (3H, s), 2.3–3.2 (2H, m), 2.45 (2H, d), 2.90 (6H, s), 3.4–3.8 (1H, m), 4.3–4.6 (1H, m), 6.6–6.8 (2H, m), 6.9–7.1 (2H, m)

EXAMPLE 38

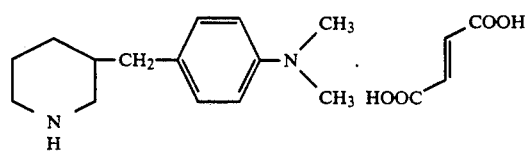

3-(4-Dimethylaminobenzyl)piperidine fumarate

The 1-acetyl-3-(4-dimethylaminobenzyl)piperidine (2.55 g) prepared in Example 37 was treated in the same manner as Example 30 to give 1.3 g of colorless crystals melting at 142° C.

Elemental analysis C₁₈H₂₆N₂O₄:
Calcd.: C, 64.65; H, 7.84; N, 8.38.
Found: C, 64.68; H, 7.75; N, 8.24.

EXAMPLE 39

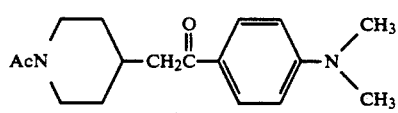

1-Acetyl-4-(4-dimethylaminobenzoylmethyl)piperidine

1) In 100 ml of thionyl chloride was dissolved 31.2 g of (N-acetylpiperidin-4-yl)acetic acid and the solution was stirred for 10 minutes. The excess thionyl chloride was then distilled off and 60 ml of fluorobenzene was added to the oily residue. Then, under ice-cooling, 42.1 g of aluminum chloride was added gradually. The mixture was stirred at room temperature for 3 hours, at the end of which time the reaction product was poured in ice-water and extracted with ethyl acetate. The extract was dried and the solvent was distilled off to give 30 g of 1-acetyl-4-(4-fluorobenzoylmethyl)piperidine as a brown oil.

2) A mixture of 1.84 g of 1-acetyl-4-(4-fluorobenzoylmethyl)piperidine and 6 ml of a 50% aqueous solution of dimethylamine was stirred at room temperature for 3 days and the reaction mixture was worked up as in Example 1 to give 1.8 g of colorless crystals melting at 136° C.

Elemental analysis $C_{17}H_{24}N_2O_2$:
Calcd.: C, 70.80; H, 8.39; N, 9.71.
Found: C, 70.85; H, 8.43; N, 9.79.

EXAMPLE 40

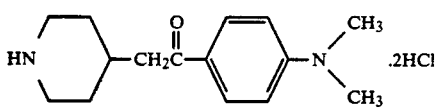

4-(4-Dimethylaminobenzoylmethyl)piperidine dihydrochloride

In 30 ml of concentrated hydrochloric acid was dissolved 1.73 g of the 1-acetyl-4-(4-dimethylaminobenzoylmethyl)piperidine prepared in Example 39 and the mixture was stirred at 100° C. for 15 hours. The solvent was then distilled off and the residue was recrystallized from ethanol-ethyl acetate to give 1.7 g of colorless crystals melting at 251°–255° C.

Elemental analysis $C_{15}H_{24}Cl_2N_2O$:
Calcd.: C, 56.43; H, 7.58; N, 8.77.
Found: C, 56.25; H, 7.47; N, 8.80.

EXAMPLE 41

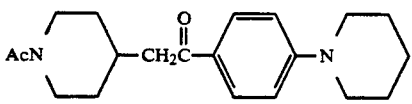

1-Acetyl-4-(4-piperidinobenzoylmethyl)piperidine

A mixture consisting of 1.84 g of 1-acetyl-4-(4-fluorobenzoylmethyl)piperidine and 5 ml of piperidine was stirred under heating at 100° C. for 20 hours. After completion of the reaction, the reaction mixture was diluted with a saturated aqueous solution of sodium hydrogen carbonate and extracted with ethyl acetate. After drying, the solvent was ditilled off and the oily residue was purified by silica gel column chromatography (eluent: ehtyl acetate) to give 2.2 g of a pale yellow oil.

Elemental analysis $C_{20}H_{28}N_2O_2$:
Calcd.: C, 73.14; H, 8.59; N, 8.53.
Found: C, 72.98; H, 8.45; N, 8.38.

EXAMPLE 42

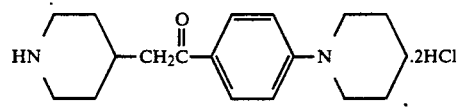

4-(4-Piperidinobenzoylmethyl)piperidine dihydrochloride

The 1-acetyl-4-(4-piperidinobenzoylmethyl)piperidine (1.71 g) prepared in Example 41 was treated in the same manner as Example 10 to give 1.93 g of colorless crystals melting at 228°–234° C.

Elemental analysis $C_{18}H_{28}Cl_2N_2O$:
Calcd.: C, 60.16; H, 7.85; N, 7.80.
Found: C, 59.91; H, 7.65; N, 7.71.

EXAMPLE 43

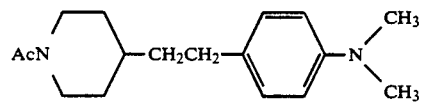

1-Acetyl-4-[2-(4-dimethylaminophenyl)ethyl]piperidine

The 1-acetyl-4-(4-dimethylaminobenzoylmethyl)piperidine (1.1 g) prepared in Example 39 was treated in the same manner as Example 15 to give 0.7 g of colorless crystals melting at 49°–51° C.

Elemental analysis $C_{17}H_{26}N_2O$:
Calcd.: C, 74.41; H, 9.55; N, 10.21.
Found: C, 74.58; H, 9.64; N, 10.09.

EXAMPLE 44

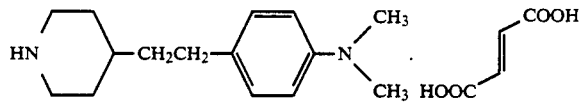

4-[2-(4-Dimethylaminophenyl)ethyl]piperidine fumarate

The 1-acetyl-4-[2-(4-dimethylaminophenyl)ethyl]piperidine (0.5 g) prepared in Example 43 was treated in the same amount as Example 30 to give 0.5 g of colorless crystals melting at 182° C.

Elemental analysis $C_{19}H_{28}N_2O_4$:
Calcd.: C, 65.49; H, 8.10; N, 8.04.
Found: C, 65.32; H, 7.95; N, 8.17.

EXAMPLE 45

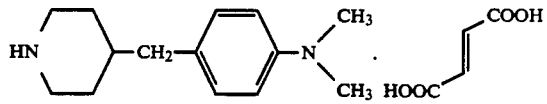

4-(4-Dimethylaminobenzyl)piperidine fumarate

The 4-(4-dimethylaminobenzyl)piperidine dihydrochloride prepared in Example 20 was treated in the per se conventional manner to give the corresponding fumarate. (Recrystallization from ethanol gave colorless crystals melting at 178°-180° C.).

Elemental analysis $C_{18}H_{26}N_2O_4$:
Calcd.: C, 64.65; H, 7.84; N, 8.38.
Found: C, 64.94; H, 7.72; N, 8.50.

EXAMPLE 46

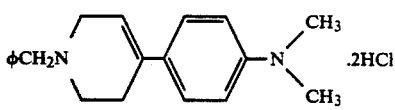

1-Benzyl-4-(4-dimethylaminophenyl)-1,2,3,6-tetrahydropyridine dihydrochloride

A solution of 10 g of p-bromo-N,N-dimethylaniline in 100 ml of tetrahydrofuran was chilled to −78° C., followed by addition of a hexane solution containing an equimolar amount of n-butyllithium. The mixture was stirred at −78° C. for 10 minutes, after which 9.5 g of N-benzyl-4-piperidone was added. The mixture was further stirred for 1 hour. The reaction mixture was then diluted with 100 ml of saturated aqueous sodium chloride solution and the organic layer was taken. From this layer, the solvent was distilled off, and 200 ml of concentrated hydrochloric acid was added to the oily residue. The mixture was heated at 100° C. with stirring for 6 hours. Finally, the solvent was distilled off and the residue was recrystallized from methanol to give 14 g of colorless crystals melting at 229°-232° C.

Elemental analysis $C_{20}H_{26}Cl_2N_2$:
Calcd.: C, 65.75; H, 7.17; N, 7.67.
Found: C, 65.49; H, 7.03; N, 7.74.

EXAMPLE 47

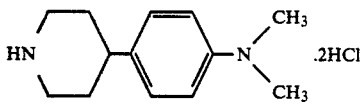

4-(4-Dimethylaminophenyl)piperidine dihydrochloride

1-Benzyl-4-(4-dimethylaminophenyl)-1,2,3,6-tetrahydropyridine dihydrochloride (3.65 g) prepared in Example 46 was dissolved in a solvent mixture of 20 ml of ethanol and 5 ml of water. Using 10% palladium-on-carbon as the catalyst, the mixture was subjected to catalytic reduction at atmospheric temperature and pressure for 10 hours. The catalyst was then filtered off and the solvent was distilled off. The residual oil was diluted with a saturated aqueous solution of sodium chloride, made basic by addition of solid sodium hydrogen carbonate and extracted with acetonitrile. The extract was dried and 5 ml of 2N-ethanolic hydrochloric acid was added. Finally the solvent was distilled off and the residue was recrystallized from ethanol to give 1.2 g of colorless crystals melting at 215°-220° C.

Elemental analysis $C_{13}H_{22}Cl_2N_2$:
Calcd.: C, 56.32; H, 8.00; N, 10.10.
Found: C, 56.41; H, 7.86; N, 9.85.

EXAMPLE 48

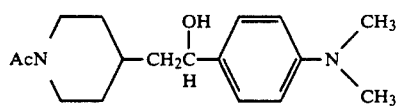

1-Acetyl-4-[2-hydroxy-2-(4-dimethylaminophenyl)ethyl]piperidine

In a solvent mixture of 60 ml of ethanol and 30 ml of water was dissolved 2.93 g of 1-acetyl-4-(4-dimethylaminobenzoylmethyl)piperidine prepared in Example 39, and at room temperature, 1 g of sodium borohydride was gradually added. The reaction mixture was diluted with dichloromethane and water for distribution and the dichloromethane layer was dried over anhydrous magnesium sulfate. The solvent was then distilled off and the oily residue was purified by silica gel column chromatography (eluent: ethyl acetate) to give a pale yellow solid melting at 119°-120° C.

Elemental analysis $C_{17}H_{26}N_2O_2$:
Calcd.: C, 70.31; H, 9.02; N, 9.65.
Found: C, 70.17; H, 9.03; N, 9.62.

EXAMPLE 49

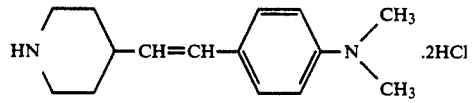

4-[2-(4-dimethylaminophenyl)ethyleny]piperidine dihydrochloride

In a solvent mixture of 2 ml of concentrated hydrochloric acid, 2 ml of water and 10 ml of ethanol was dissolved 1.0 g of the 1-acetyl-4-[2-hydroxy-2-(4-dimethylaminophenyl)ethyl]piperidine prepared in Example 48 and the mixture was heated at 100° C. with stirring for 15 hours. The solvent was then distilled off and the residue was recrystallized from ethanol-ethyl acetate to give 0.6 g of colorless crystals melting at 220°-245° C.

Elemental analysis $C_{15}H_{24}Cl_2N_2$:
Calcd.: C, 59.41; H, 7.98; N, 9.24.
Found: C, 59.70; H, 7.19; N, 8.98.

EXAMPLE 50

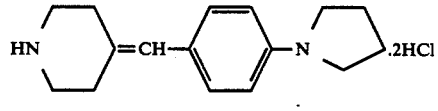

4-(4-Pyrrolidinobenzylidene)piperidine dihydrochloride

The 1-acetyl-4-(4-pyrrolidinobenzoyl)piperidine (2.0 g; Compound 13) prepared in Example 4 was treated in the same manner as Example 44 to give 1-acetyl-4-(α-hydroxy-4-pyrrolidinobenzyl)piperidine (1.2 g), which was then worked up as in Example 49 to give 1.1 g of an amorphous solid.

Elemental analysis $C_{16}H_{24}Cl_2N_2$:
Calcd.: C, 60.95; H, 7.67; N, 8.88.
Found: C, 60.75; H, 7.61; N, 8.76.

EXAMPLE 51

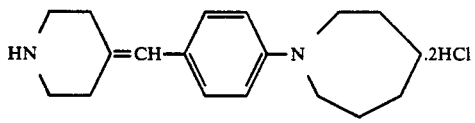

4-(4-Homopiperidinobenzylidene)piperidine dihydrochloride

The 1-acetyl-4-(4-homopiperidinobenzoyl)piperidine (2.0 g; Compound No. 14) prepared in Example 4 was treated in the same manner as Example 50 to give 1.3 g of a colorless amorphous solid.

Elemental analysis $C_{18}H_{28}Cl_2N_2$:
Calcd.: C, 62.97; H, 8.22; N, 8.16.
Found: C, 62.67; H, 8.13; N, 8.04.

EXAMPLE 52

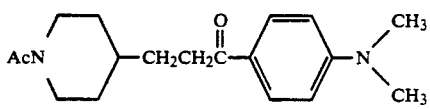

1-Acetyl-4-[2-(4-dimethylaminobenzoyl)ethyl]piperidine

1) In 300 ml of acetic acid was dissolved 33 g of ethyl β-(pyridin-4-yl)acrylate, and using platinum oxide as the catalyst, catalytic reduction was carried out at 70°–80° C. under atmospheric pressure. After addition of 40 ml of acetic anhydride, the catalyst was filtered off and the solvent was removed under reduced pressure. The residue was dissolved in water and neutralized with potassium carbonate and the product was extracted into dichloromethane. The extract was dried over anhydrous sodium sulfate and the solvent was then distilled off to give 44.8 g of an oil.

2) In 200 ml of methanol was dissolved 42.9 g of the above oil, followed by addition of a solution of 12.7 g of potassium hydroxide in 20 ml of water. The mixture was stirred at 50° C. for 1.5 hours and at room temperature for 12 hours. The reaction mixture was then neutralized with concentrated hydrochloric acid and the solvent was distilled off. The residue was diluted with methanol and the insolubles were filtered off. The filtrate was then concentrated and the resulting crude crystals were collected by filtration to give 27 g of (N-acetylpiperidin-4-yl)propionic acid melting at 201°–206° C.

3) Using 26.7 g of (N-acetylpiperidin-4-yl)propionic acid, the procedure of Example 39 was repeated to give 26.1 g of 1-acetyl-4-[2-(4-fluorobenzoyl)ethyl]piperidine as colorless crystals melting at 95°–96° C.

Elemental analysis $C_{16}H_{20}FNO_2$:
Calcd.: C, 69.29; H, 7.27; N, 5.05.
Found: C, 69.16; H, 7.36; N, 4.99.

4) A mixture consisting of 3.2 g of 1-acetyl-4-[2-(4-fluorobenzoyl)ethyl]piperidine and 10 ml of 50% aqueous dimethylamine solution was heated at 100° C. with stirring for 6 hours and then worked up in the same manner as Example 37 to give 1.6 g of colorless crystals melting at 158°–160° C.

Elemental analysis $C_{18}H_{26}N_2O_2$:
Calcd.: C, 71.49; H, 8.67; N, 9.26.
Found: C, 71.54; H, 8.86; N, 9.15.

EXAMPLE 53

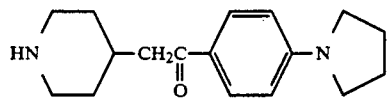

4-(4-Pyrrolidinobenzoylmethyl)piperidine

1-Acetyl-4-(4-pyrrolidinobenzoylmethyl)piperidine (1.0 g) prepared in the same manner as Example 41 was treated in the same manner as Example 10 to give the corresponding hydrochloride, which was dissolved in a saturated aqueous solution of sodium chloride. The solution was made basic by addition of solid sodium hydrogen carbonate and extracted with acetonitrile. The extract was dried and the solvent was distilled off. The residue was recrystallized from ethyl acetate to give 0.7 g of a colorless solid melting at 144°–145° C.

Elemental analysis $C_{17}H_{24}N_2O$:
Calcd.: C, 74.96; H, 8.88; N, 10.28.
Found: C, 75.06; H, 8.62; N, 10.37.

EXAMPLE 54

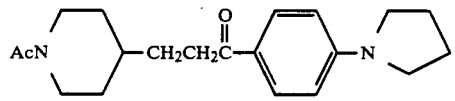

1-Acetyl-4-[2-(4-pyrrolidinobenzoyl)ethyl]piperidine

Using 3.2 g of 1-acetyl-4-[2-(4-fluorobenzoyl)ethyl]piperidine and 6 ml of pyrrolidine, the procedure of Example 53 was repeated to give 2.7 g of a colorless oil.

Elemental analysis $C_{20}H_{28}N_2O_2$:
Calcd.: C, 73.14; H, 8.59; N, 8.53.
Found: C, 73.19; H, 8.40; N, 8.34.

EXAMPLE 55

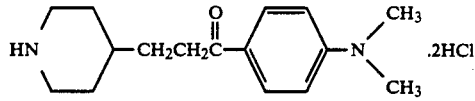

4-[2-(4-Dimethylaminobenzoyl)ethyl]piperidine dihydrochloride

The 1-acetyl-4-[2-(4-dimethylaminobenzoyl)ethyl]piperidine prepared in Example 53 was treated in the same manner as Example 10 to give a white solid melting at 182°–183° C.

Elemental analysis $C_{16}H_{26}Cl_2N_2O$:
Calcd.: C, 57.66; H, 7.86; N, 8.40.
Found: C, 57.53; H, 7.86; N, 8.49.

EXAMPLE 56

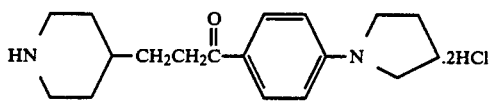

4-[2-(4-Pyrrolidinobenzoyl)ethyl]piperidine dihydrochloride

The 1-acetyl-4-[2-(4-pyrrolidinobenzoyl)ethyl]piperidine prepared in Example 54 was treated in the same manner as Example 10 to give colorless crystals melting at 207°–209° C.

Elemental analysis $C_{18}H_{28}Cl_2N_2O$:
Calcd.: C, 60.16; H, 7.85; N, 7.80.
Found: C, 60.22; H, 7.70; N, 7.71.

EXAMPLE 57

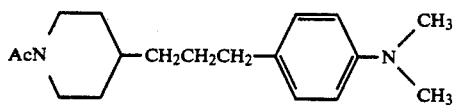

1-Acetyl-4-[3-(4-dimethylaminophenyl)propyl]piperidine

The 1-acetyl-4-[2-(4-dimethylaminobenzoyl)ethyl]piperidine (3.6 g) prepared in Example 52 was treated in the same manner as Example 15 to give 2.6 g of a colorless oil.

NMR (CDCl$_3$): δ0.8–1.8 (9H, m), 2.06 (3H, s), 2.5–2.7 (1H, m), 2.47 (2H, t), 2.7–3.2 (1H, m), 2.85 (6H, s), 3.6–3.9 (1H, m), 4.4–4.7 (1H, m), 6.6–6.8 (2H, m), 6.9–7.1 (2H, m)

EXAMPLE 58

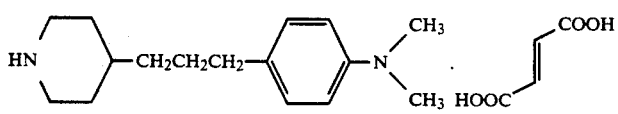

The 1-acetyl-4-[3-(4-dimethylaminophenyl)propyl]piperidine (2.4 g) prepared in Example 57 was treated in the same manner as Example 30 to give 1.6 g of colorless crystals melting at 158°–160° C.

Elemental analysis $C_{20}H_{30}N_2O_4$:
Calcd.: C, 66.27; H, 8.34; N, 7.73.
Found C, 66.23; H, 8.17; N, 7.74.

EXAMPLE 59

1-Benzyl-4-[2-(4-pyrrolidinobenzoyl)ethyl]piperidine

1) The 1-acetyl-4-[2-(4-fluorobenzoyl)ethyl]piperidine (10 g) prepared in Example 52 was dissolved in 50 ml of concentrated hydrochloric acid and the solution was heated at 100° C. overnight. The solvent was then distilled off and the residue was recrystallized from methanol-ether to give 9.13 g of colorless crystals melting at 188°–191° C.

2) The crystals (5.60 g) obtained above were dissolved in 30 ml of dioxane, followed by addition of 4.07 g of benzyl bromide and 3.45 g of potassium carbonate. The mixture was heated at 90° C. for 3 hours and the solvent was distilled off. The residue was diluted with water and extracted with ether, and the organic layer was washed with water and dried. The solvent was distilled off and the residue was recrystallized from dichloromethane-n-hexane to give 6.72 g of 1-benzyl-4-[2-(4-fluorobenzoyl)ethyl]piperidine as colorless crystals melting at 65°–67° C.

Elemental analysis $C_{21}H_{24}FNO$:
Calcd.: C, 77.51; H, 7.43; N, 4.30.
Found: C, 77.74; H, 7.47; N, 4.32.

3) A mixture consisting of 0.5 g of 1-benzyl-4-[2-(4-fluorobenzoyl)ethyl]piperidine and 2 ml of pyrrolidine was heated at 150° C. for 24 hours and the reaction mixture was subjected to distribution between ethyl acetate and saturated aqueous sodium hydrogen carbonate solution. The organic layer was dried and the solvent was distilled off. The residue was recrystallized from ethyl acetate to give 0.7 g of colorless crystals melting at 144°–145° C.

Elemental analysis $C_{25}H_{32}N_2O$:
Calcd.: C, 79 75; H, 8.57; N, 7.44.
Found: C, 79.54; H, 8.56; N, 7.46.

EXAMPLE 60

The compounds shown in Table 6 were prepared in substantially the same manner as Example 59.

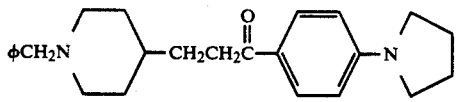

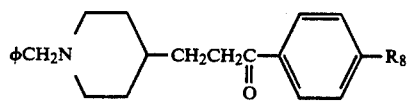

TABLE 6

| Compound No. | R$_8$ | Melting point (°C.) | Molecular formula | Elemental analysis Calcd. (Found) | | |
|---|---|---|---|---|---|---|
| | | | | C | H | N |
| 1 | (piperidinyl) | 133–136 | $C_{26}H_{34}N_2O$ | 79.96 (79.61 | 8.77 8.72 | 7.14 7.13) |

TABLE 6-continued

φCH₂N⟨piperidine⟩—CH₂CH₂C(=O)—C₆H₄—R₈

| Compound No. | R₈ | Melting point (°C.) | Molecular formula | Elemental analysis Calcd. (Found) | | |
|---|---|---|---|---|---|---|
| | | | | C | H | N |
| 2 | azepan-1-yl (7-membered N ring) | 95–97 | $C_{27}H_{36}N_2O$ | 80.15 (79.96 | 8.97 9.03 | 6.92 6.81) |
| 3 | N(CH₃)₂ | 97–99 | $C_{23}H_{30}N_2O$ | 78.82 (78.85 | 8.63 8.63 | 7.99 7.95) |
| 4 | NH(C₂H₅) | 99–101 | $C_{23}H_{30}N_2O$ | 78.82 (78.61 | 8.63 8.73 | 7.99 7.78) |
| 5 | morpholino | 136–139 | $C_{25}H_{32}N_2O_2$ | 76.50 (76.19 | 8.22 8.29 | 7.14 6.87) |
| 6 | imidazol-1-yl | 109–112 | $C_{24}H_{27}N_3O$ | 77.18 (77.02 | 7.29 7.21 | 11.25 11.20) |
| 7 | 4-methylpiperazin-1-yl | 113–114 | $C_{26}H_{35}N_3O$ | 77.00 (76.84 | 8.70 8.74 | 10.36 10.20) |
| 8 | NH(CH₃) | 62–66 | $C_{22}H_{28}N_2O$ | 78.53 (78.50 | 8.39 8.32 | 8.33 8.35) |
| 9 | 4-acetylpiperazin-1-yl | 157–159 | $C_{27}H_{35}N_3O_2$ | 74.79 (74.70 | 8.14 8.15 | 9.69 9.63) |
| 10 | pyrrolidin-1-yl | 214–217 | $C_{25}H_{32}N_2O\cdot HCl$ | 72.71 (72.65 | 8.05 8.07 | 6.78 6.78) |
| 11 | pyrrolidin-1-yl | 215–217 | $C_{25}H_{32}N_2O\cdot 2HCl$ | 66.81 (66.65 | 7.62 7.57 | 6.23 6.14) |
| 12 | pyrrolidin-1-yl | 222–224 | $C_{25}H_{32}N_2O\cdot C_4H_4O_4$* | 70.71 (70.55 | 7.37 7.33 | 5.69 5.68) |
| 13 | N(CH₃)₂ | 190–191 | $C_{23}H_{30}N_2O\cdot C_4H_4O_4$* | 69.51 (69.59 | 7.34 7.40 | 6.00 5.95) |

TABLE 6-continued

φCH₂N—[piperidine]—CH₂CH₂C(=O)—[phenyl]—R₈

| Compound No. | R₈ | Melting point (°C.) | Molecular formula | Elemental analysis Calcd. (Found) | | |
|---|---|---|---|---|---|---|
| | | | | C | H | N |
| 14 | N‾‾NCH₃ | 162–163 | C₂₆H₃₅N₃O.2C₄H₄O₄* | 64.04 (63.96 | 6.80 6.71 | 6.59 6.53) |
| 15 | N‾‾ | 224–225 | C₂₆H₃₄N₂O.C₄H₄O₄* | 71.12 (70.96 | 7.56 7.53 | 5.53 5.60) |
| 16 | N‾‾NH | 135–137 | C₂₅H₃₃N₃O | 76.69 (75.51 | 8.49 8.46 | 10.73 10.65) |
| 17 | N‾‾NH | 188–190 | C₂₅H₃₃N₃O.C₄H₄O₄* | 68.62 (68.48 | 7.35 7.22 | 8.28 8.19) |
| 18 | N‾‾NCH(φ)(φ) | 129–130 | C₃₈H₄₃N₃O | 81.83 (81.72 | 7.77 7.69 | 7.53 7.50) |
| 19 | N‾‾NAc | 151–152 | C₂₇H₃₅N₃O₂.C₄H₄O₄* | 67.74 (67.64 | 7.15 7.08 | 7.64 7.62) |
| 20 | N‾‾O | 203–205 | C₂₅H₃₂N₂O₂.C₄H₄O₄* | 68.48 (68.26 | 7.13 7.25 | 5.51 5.60) |
| 21 | N‾‾NCH(φ)(φ) | 194–196 | C₃₈H₄₃N₃O.C₄H₄O₄* | 74.86 (74.59 | 7.03 7.15 | 6.24 6.19) |
| 22 | NHCH₂CH₂N‾‾ | 67–69 | C₂₈H₃₉N₃O | 77.56 (77.58 | 9.07 9.19 | 9.69 9.67) |
| 23 | N(CH₃)(H) | 140–142 | C₂₂H₂₈N₂O.C₄H₄O₄* | 69.01 (68.92 | 7.13 7.18 | 6.19 6.10) |
| 24 | N(C₂H₅)(C₂H₅) | 159–161 | C₂₅H₃₄N₂O.C₄H₄O₄* | 70.42 (70.24 | 7.74 7.66 | 5.66 5.61) |

*C₄H₄O₄ denotes fumaric acid

EXAMPLE 61

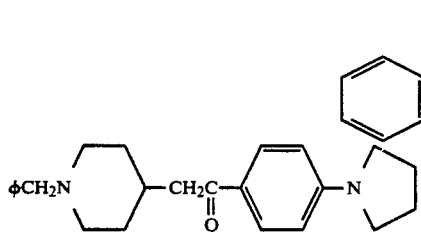

1-Benzyl-4-[4-pyrrolidinobenzoylmethyl]piperidine

Using 2.0 g of the 4-(4-pyrrolidinobenzoylmethyl)-piperidine prepared in Example 53, the benzylation procedure of Example 59-2) was repeated to give 1.8 g of colorless crystals melting at 110°-112° C.

Elemental analysis C$_{24}$H$_{30}$N$_2$O:
Calcd.: C, 79.52; H, 8.34; N, 7.73.
Found: C, 79.55; H, 8.35; N, 7.77.

EXAMPLE 62

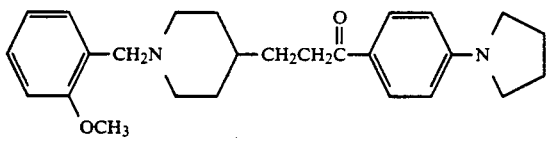

1-o-Methoxybenzyl-4-[2-(4-pyrrolidinobenzoyl)ethyl]-piperidine

Using the 4-[2-(4-pyrrolidinobenzoyl)ethyl]piperidine dihydrochloride prepared in Example 56 and p-methoxybenzyl bromide, the p-methoxybenzylation procedure of Example 59 was repeated to give colorless crystals melting at 89°-91° C.

Elemental analysis C$_{26}$H$_{34}$N$_2$O$_2$:
Calcd.: C, 76.81; H, 8.43; N, 6.89.
Found: C, 76.64; H, 8.48; N, 6.83.

EXAMPLE 63

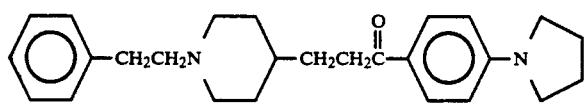

1-[(2-Phenyl)ethyl]-4-[2-(4-pyrrolidinobenzoyl)ethyl]-piperidine

In the same manner as Example 59, the title compound was obtained as colorless crystals melting at 102°-103° C.

Elemental analysis C$_{26}$H$_{34}$N$_2$O:
Calcd.: C, 79.96; H, 8.77; N, 7.17.
Found: C, 79.75; H, 8.86; N, 7.02.

EXAMPLE 64

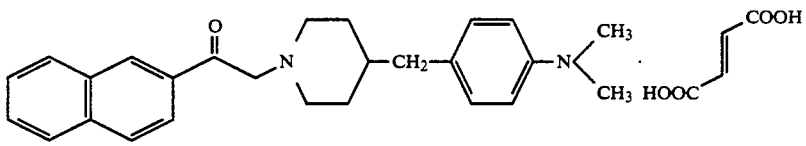

[1-[(Naphtho-2-yl)carbonylmethyl]-4-(4-dimethylaminobenzoyl)]piperidine fumarate The 4-(4-dimethylaminobenzoyl)piperidine dihydrochloride (Compound No. 5) prepared in Example 11 was treated with ethyl acetate and aqueous sodium hydroxide solution to give free 4-(4-dimethylaminobenzoyl)piperidine, and 2.04 g of this compound and 2.19 g of 2-bromoacetylnaphthalene were dissolved in n-butanol (30 ml). To this solution were added 0.2 g of potassium iodide and 2.95 g of sodium hydrogen carbonate and the mixture was heated at 100° C. with stirring for 3 hours. The solvent was then distilled off and the residue was diluted with water (50 ml) and extracted with chloroform. The solvent was then distilled off. The oily residue was purified by silica gel column chromatography (eluent: methanol-dichloromethane= 1:19, v/v) and the solvent was removed. After the remaining oil was dissolved in methanol, 0.51 g of fumaric acid was added and dissolved and the solvent was distilled off. Finally the residue was recrystallized from ethanol to give 3.0 g of colorless crystals melting at 170°-185° C. (decomp.)

Elemental analysis C$_{30}$H$_{32}$N$_2$O$_6$:
Calcd.: C, 69.75; H, 6.24; N, 5.42.
Found: C, 69.80; H, 6.15; N, 5.56.

EXAMPLE 65

[1-[(Naphtho-2-yl)carbonylmethyl]-4-(4-dimethylaminobenzyl)]-piperidine fumarate Using the 4-(4-dimethylaminobenzyl)piperidine dihydrochloride prepared in Example 20, the procedure of Example 64 was repeated to give colorless crystals melting at 190°-193° C.

Elemental analysis C$_{30}$H$_{34}$N$_2$O$_5$:
Calcd.: C, 71.69; H, 6.82; N, 5.57.
Found: C, 71.54; H, 6.87; N, 5.46.

EXAMPLE 66

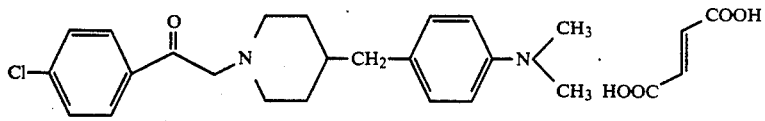

[1-(4-Chlorobenzoylmethyl)-4-(4-dimethylaminobenzyl)]piperidine fumarate

The 4-(4-dimethylaminobenzyl)piperidine dihydrochloride prepared in Example 20 was converted to the free compound as in Example 64, and 3.27 g of the resulting 4-(4-dimethylaminobenzyl)piperidine and 2.8 ml of triethylamine were dissolved in dioxane (20 ml). This solution was added dropwise to a dioxane solution (30 ml) containing 3.5 g of p-chlorophenacyl bromide and the mixture was stirred at room temperature for 10 minutes. The solvent was then distilled off and the residue was diluted with 1N-aqueous sodium hydroxide solution (20 ml) and extracted with ethyl acetate. The extract was dried over anhydrous magnesium sulfate and the solvent was distilled off. The oily residue was purified by silica gel column chromatography and, then, converted to the fumarate as in Example 64. Recrystallization of this fumarate from ethyl acetate gave 1.1 g of colorless crystals melting at 131°–132° C.

Elemental analysis $C_{26}H_{31}ClN_2O_5$:
Calcd.: C, 64.12; H, 6.42; N, 5.75.
Found: C, 64.05; H, 6.45; N, 5.83.

EXAMPLE 67

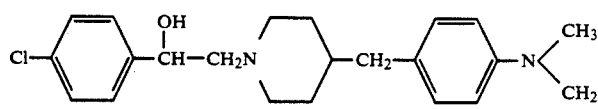

[1-[[2-(4-Chloro)phenyl-2-hydroxy]ethyl]-4-(4-dimethylaminobenzyl)]piperidine

The [1-(4-chlorobenzoylmethyl)-4-(4-dimethylaminobenzoyl)]piperidine fumarate prepared in Example 66 was converted to the free compound as in Example 64 to give [1-(4-chlorobenzoylmethyl)-4-(4-dimethylaminobenzyl)]piperidine. Then, 1.65 g of this compound was dissolved in a solvent mixture of ethanol (50 ml) and water (50 ml). To the solution was added 0.51 g of sodium borohydride gradually, which resulted in separation of precipitates. The reaction system was stirred at room temperature for 2 hours, at the end of which time the solvent was distilled off and the residue was diluted with water (100 ml) and extracted with chloroform (100 ml). The extract was dried over anhydrous magnesium sulfate and the solvent was distilled off. The residual solid was recrystallized from ethanol to give 0.8 g of colorless crystals melting at 159°–160° C.

Elemental analysis $C_{22}H_{29}ClN_2O$:
Calcd.: C, 70.85; H, 7.84; N, 7.51.
Found: C, 70.62; H, 7.83; N, 7.27.

EXAMPLE 68

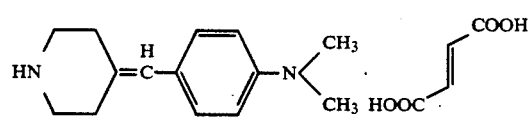

4-(4-Dimethylaminobenzylidene)piperidine fumarate

In 20 ml of benzene were suspended 1.35 g of the 4-[(α-hydroxy-4-dimethylamino)benzyl]piperidine dihydrochloride synthesized in Example 14 [Compound No. 5] and 0.6 g of aluminum chloride, and the resulting suspension was stirred at 80° C. for 24 hours. Then, 50 ml of 1N aqueous sodium hydroxide solution and 50 ml of ethyl acetate were added thereto and the organic layer was taken and dried over anhydrous magnesium sulfate. The solvent was then distilled off and the oily residue was dissolved in 20 ml of methanol. To this solution was added 0.7 g of fumaric acid and the solvent was distilled off. Finally, the residue was recrystallized from ethanol to give 1.4 g of colorless crystals melting at 181°–184° C.

Elemental analysis, $C_{18}H_{24}N_2O_4$:
Calcd.: C, 65.04; H, 7.28; N, 8.43.
Found: C, 64.92; H, 7.14; N, 8.50.

EXAMPLE 69

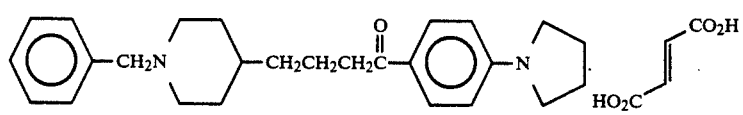

1-Benzyl-4-[3-(4-pyrrolidinobenzoyl)propyl]piperidine fumarate

1) In 160 l of acetic acid was dissolved 9 g of 4-(pyridin-4-yl)butyric acid and catalytic reduction was carried out using 1 g of platinum oxide as the catalyst at 45°–50° C. and atmospheric pressure. After addition of 100 ml of acetic anhydride, the catalyst was filtered off and the solvent was distilled off under reduced pressure. The residue was dissolved in ethanol and after 5 drops of concentrated hydrochloric acid were added, the mixture was refluxed for 1 hour. The solvent was then distilled off under reduced pressure and the residue was diluted with water, neutralized with potassium carbonate and extracted with dichloromethane. The extract was dried over anhydrous sodium sulfate and the solvent was distilled off to give 10 g of oil.

2) Using 10 g of the above oil, the procedure of Example 52-2) was repeated to give 8.1 g of 4-(N-acetyl-piperidin-4-yl)butyric acid as a viscous oil.

3) Then, using 2.15 g of 4-(N-acetylpiperidin-4yl)-butyric acid, the procedure of Example 39 was repeated to give 1.95 g of 1-acetyl-4-[3-(4-fluorobenzoyl)propyl]-piperidine as colorless crystals melting at 77°-78° C.

Elemental analysis, $C_{17}H_{22}FNO_2$:
Calcd.: C, 70.08; H, 7.61; N, 4.81.
Found C, 69.76; H, 7.65; N, 4.81.

4) A solution of 1-acetyl-4-[3-(4-fluorobenzoyl)-propyl]piperidine(1.7 g) in concentrated hydrochloric acid (15 ml) was refluxed for 16 hours and the hydrochloric acid was then distilled off under reduced pressure. The residue was dissolved in water and the solution was made weakly basic (pH ca.8) with 5% aqueous sodium hydroxide solution and extracted with dichloromethane. The extract was washed with water and dried over anhydrous sodium sulfate and the solvent was distilled off to recover 1.3 g of residue. To a solution of this residue (1.3 g) in ethanol (10 ml) was added 0.94 g of potassium carbonate and 0.9 g of benzyl bromide was added dropwise with ice-cooling. The mixture was stirred at room temperature for 2 hours and then filtered and the filtrate was concentrated under reduced pressure. The residue was diluted with water and extracted with dichloromethane and the extract was washed with water and dried over anhydrous sodium sulfate. Finally the solvent was distilled off to give 1.6 g of 1-benzyl-4-[3-(4-fluorobenzoyl)propyl]piperidine melting at 53°-55° C.

Elemental analysis, $C_{22}H_{26}FNO$:
Calcd.: C, 77.84; H, 7.72; N, 4.13.
Found: C, 77.90; H, 7.76; N, 3.84.

5) To a solution of the 1-benzyl-4-[3-(4-fluorobenzoyl)propyl]piperidine (0.6 g) synthesized in 4) in dioxane (1 ml) was added 3 ml of pyrrolidine and the mixture was heated at 100° C. for 16 hours. Thereafter, the procedure of Example 37 was repeated to give 0.58 g of 1-benzyl-4-[3-(4-pyrrolidinobenzoyl)propyl]piperidine as colorless crystals melting at 115°-116° C.

Elemental analysis $C_{26}H_{34}N_2O$
Calcd.: C, 79.96; H, 8.77; N, 7.17.
Found: C, 79.95; H, 8.83; N, 7.03.

6) The above 1-benzyl-4-[3-(4 -pyrrolidinobenzoyl)-propyl]piperidine (0.55 g) was treated with one equivalent of fumaric acid (0.16 g) and the reaction product was recrystallized from ethanol to give 0.7 g of 1-benzyl-4-[3-(4-pyrrolidinobenzoyl)propyl]piperidine fumarate as colorless crystals melting at 220°-222° C.

Elemental analysis, $C_{26}H_{34}N_2O \cdot C_4H_4O_4$:
Calcd.: C, 71.12; H, 7.56; N, 5.53.
Found: C, 71.19; H, 7.57; N, 5.53.

EXAMPLE 70

1-Benzyl-4-[3-(4-dimethylaminobenzoyl)propyl]piperidine fumarate

1) Using the 1-benzyl-4-[3-(4-fluorobenzoyl)propyl]-piperidine synthesized in Example 69-4-), the procedure of Example 69-5) was repeated to give 1-benzyl-4-[3-(4-dimethylaminobenzoyl)propyl]piperidine as colorless crystals melting at 83°-85° C.

Elemental analysis, $C_{24}H_{32}N_2O$:
Calcd.: C, 79.08; H, 8.85; N, 7.69.
Found: C, 79.01; H, 8.72; N, 7.55.

2) The compound obtained in 1) was treated with one equivalent of fumaric acid and the reaction product was crystallized from ethanol to give 1-benzyl-4-[3-(4-fluorobenzoyl)propyl]piperidine fumarate as colorless crystals melting at 210°-211° C.

Elemental analysis, $C_{24}H_{32}N_2O \cdot C_4H_4O_4$:
Calcd. C, 69.98; H, 7.55; N, 5.83.
Found: C, 69.71; H, 7.44; N, 5.62.

EXAMPLE 71

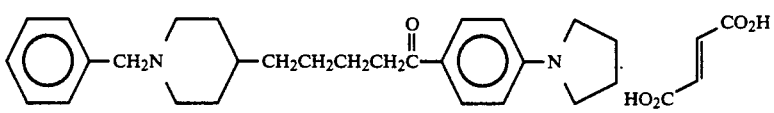

1-Benzyl-4-[4-(4-pyrrolidinobenzoyl)butyl]piperidine fumarate

1) To an ethanolic solution of sodium ethoxide prepared from 1.4 g of sodium and 200 ml of ethanol were added 5.36 g of pyridin-4-aldehyde and 27 g of (3-methoxycarbonyl-2-propenyl)triphenylphosphonium bromide and the mixture was allowed to stand at room temperature for 3 days. The solvent was then distilled off under reduced pressure and the residue was dissolved in water and acidified with 10% hydrochloric acid (pH ca. 5). The solution was washed with ethyl acetate and the aqueous layer was made basic (pH ca. 8) with 10% aqueous sodium hydroxide solution and extracted with dichloromethane. The extract was dried over anhydrous sodium sulfate and the solvent was distilled off under reduced pressure to give 7.0 g of methyl 5-(pyridin-4-yl)-2,4-pentadienoate as oil.

2) Using 7.0 g of methyl 5-(pyridin-4-yl)-2,4-pentadienoate, the procedure of Example 69-1) and 2) was repeated to give 6.5 g of 5-(N-acetylpiperidin-4-yl)valeric acid as hygroscopic crystals melting at 198°-203° C.

3) Using 2.3 g of 5-(N-acetylpiperidine-4-yl)valeric acid prepared in 2), the procedure of Example 39 was repeated to give 1.6 g of 1-acetyl-4-[4-(4-fluorobenzoyl)butyl]piperidine as colorless crystals melting at 98°-100° C.

Elemental analysis, $C_{18}H_{24}FNO_2$:
Calcd.: C, 70.79; H, 7.92; N, 4.59.
Found: C, 70.75; H, 7.88; N, 4.60.

4) Using 1.5 g of 1-acetyl-4-[4-(4-fluorobenzoyl)-butyl]piperidine, the procedure of Example 69-4) was repeated to give 1.45 g of 1-benzyl-4-[4-(4-fluoroben-

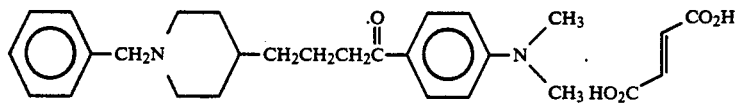

zoyl)butyl]piperidine as colorless crystals melting at 67°–68° C.

Elemental analysis, C₂₃H₂₈FNO:
Calcd.: C, 78.15; H, 7.98; N, 3.96.
Found: C, 78.06; H, 7.78; N, 3.83.

5) Using 0.6 g of the 1-benzyl-4-[4-(4-fluorobenzoyl)butyl]piperidine prepared in 4), the procedure of Example 69-5) was repeated to give 0.57 g of 1-benzyl-4-[4-(4-pyrrolidinobenzoyl)butyl]piperidine as colorless crystals melting at 129°–131° C.

Elemental analysis, C₂₇H₃₆N₂O:
Calcd C, 80.15; H, 8.97; N, 6.92.
Found: C, 80.04; H, 8.89; N, 6.85.

6) The 1-benzyl-4-[4-(4-pyrrolidinobenzoyl)butyl]piperidine (0.5 g) prepared in 5) was treated with one equivalent of fumaric acid (0.14 g) and the reaction product was crystallized from ethanol to give 0.6 g of 1-benzyl-4-[4-(4-pyrrolidinobenzoyl)butyl]piperidine fumarate as colorless crystals melting at 183°–185° C.

Elemental analysis, C₂₇H₃₆N₂O·C₄H₄O₄:
Calcd.: C, 71.51; H, 7.74; N, 5.38.
Found: C, 71.45; H, 7.85; N, 5.23.

EXAMPLE 72

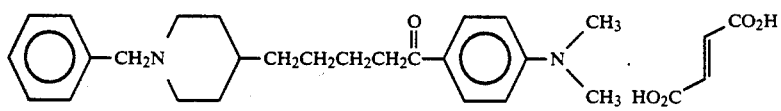

1-Benzyl-4-[4-(4-dimethylaminobenzoyl)butyl]piperidine fumarate

1) Using the 1-benzyl-4-[4-(4-fluorobenzoyl)butyl]piperidine synthesized in Example 71-4), the procedure of Example 69-5) was repeated to give 1-benzyl-4-[4-(4-dimethylaminobenzoyl)butyl]piperidine as colorless crystals melting at 121°–123° C.

Elemental analysis, C₂₅H₃₄N₂O:
Calcd.: C, 79.32; H, 9.05; N, 7.40.
Found: C, 79.09; H, 8.98; N, 7.27.

2) The compound obtained in 1) was treated with one equivalent of fumaric acid and the reaction product was crystallized from ethanol to give 1-benzyl-4-[4-(4-dimethylaminobenzoyl)butyl]piperidine fumarate as colorless crystals melting at 143°–145° C.

Elemental analysis, C₂₅H₃₄N₂O·C₄H₄O₄:
Calcd.: C, 70.42; H, 7.74; N, 5.66.
Found: C, 70.29; H, 7.64; N, 5.49.

EXAMPLE 73

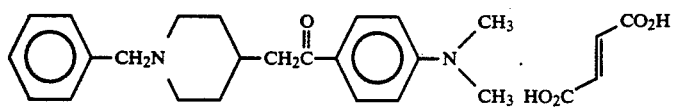

1-Benzyl-4-(4-dimethylaminobenzoylmethyl)piperidine fumarate

The 4-(4-dimethylaminobenzoylmethyl)piperidine dihydrochloride (0.55 g) obtained in Example 40 was benzylated by the same procedure as Example 59-2), followed by treatment with one equivalent of fumaric acid, to give 0.7 g of colorless crystals melting at 245°–247° C.

Elemental analysis, C₂₂H₂₈N₂O·C₄H₄O₄:
Calcd.: C, 69.01; H, 7.13; N, 6.19.
Found: C, 68.95; H, 7.04; N, 6.05.

EXAMPLE 74

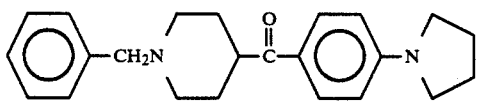

1-Benzyl-4-(4-pyrrolidinobenzoyl)piperidine

The 4-(4-pyrrolidinobenzoyl)piperidine dihydrochloride prepared in Example 11-1) (0.66 g) was benzylated by the same procedure as described in Example 59-2) to give 0.5 g of colorless crystals melting at 154°–156° C.

Elemental analysis, C₂₃H₂₈N₂O:
Calcd.: C, 79.27; H, 8.10; N, 8.04.
Found: C, 79.23; H, 8.03; N, 8.03.

EXAMPLE 75

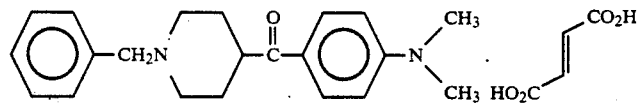

1-Benzyl-4-(4-dimethylaminobenzoyl)piperidine fumarate

The 4-(4-dimethylaminobenzoyl)piperidine dihydrochloride synthesized in Example 11-5) was benzylated by the same procedure as described in Example 59-2) and, then, treated with one equivalent of fumaric acid to give colorless crystals melting at 175°–178° C.

Elemental analysis, C₂₁H₂₆N₂O·C₄H₄O₄:
Calcd.: C, 68.47; H, 6.90; N, 6.39.
Found: C, 68.35; H, 6.74; N, 6.32.

EXAMPLE 76

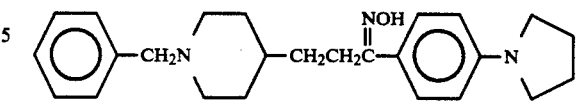

1-Benzyl-4-[3-hydroxyimino-3-(4-pyrrolidinophenyl)-propyl]piperidine

To a mixed solution (20 ml) containing 0.8 g of the 1-benzyl-4-[2-(4-pyrrolidinobenzoyl)ethyl]piperidine prepared in Example 59 and 0.7 g of hydroxylamine hydrochloride in ethanol was added a solution (7 ml) of 1.4 g of potassium hydroxide in methanol dropwise with warming at 50°–55° C. The mixture was further heated at 50°–55° C. for one hour, at the end of which time it was added to 200 ml of ice-water. The resulting precipitate was collected by filtration, rinsed and dissolved in dichloromethane. The solution was dried over anhydrous sodium sulfate and the solvent was distilled off under reduced pressure to give crude crystals. Recrystallization from dichloromethane-ether yielded 0.55 g of colorless crystals melting at 153°–158° C.

Elemental analysis, $C_{25}H_{33}N_3O$:
Calcd.: C, 76.69; H, 8.50; N, 10.73.
Found: C, 76.53; H, 8.43; N, 10.65.

EXAMPLE 77

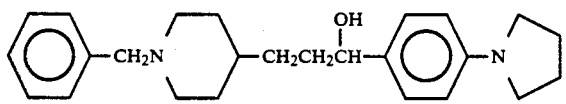

1-Benzyl-4-[3-hydroxy-3-(4-pyrrolidinophenyl)propyl]piperidine

To a solution (10 ml) of 0.6 g of lithium aluminum hydride (0.6 g) in tetrahydrofuran was added 0.6 g of the 1-benzyl-4-[2-(4-pyrrolidinobenzoyl)ethyl]piperidine synthesized in Example 59 and the mixture was stirred at room temperature for 30 minutes. Then, water was added cautiously thereto for decomposing the excess reagent and the reaction product was then extracted into dichloromethane. The extract was dried over anhydrous sodium sulfate and the solvent was distilled off under reduced pressure to give crude crystals. Recrystallization from ether-hexane yielded 0.5 g of colorless crystals melting at 93°–95° C.

Elemental analysis, $C_{25}H_{34}N_2O$:
Calcd.: C, 79.32; H, 9.05; N, 7.40.
Found: C, 79.04; H, 9.18; N, 7.24.

EXAMPLE 78

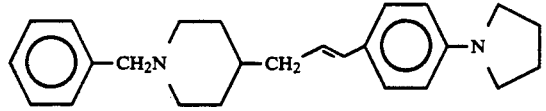

(E)-1-Benzyl-4-[3-(4-pyrrolidinophenyl)-2-propen-1-yl]piperidine

To an ethanolic solution (10 ml) of 0.3 g of the 1-benzyl-4-[3-hydroxy-3-(4-pyrrolidinophenyl)propyl]piperidine synthesized in Example 77 was added one drop of concentrated hydrochloric acid and the mixture was refluxed for 30 minutes. The solvent was then distilled off under reduced pressure and the residue was dissolved in dichloromethane. The solution was washed with water and dried over anhydrous sodium sulfate and the solvent was distilled off under reduced pressure to give crude crystals. Recrystallization from hexane yielded 0.25 g of colorless crystals melting at 115°–117° C.

Elemental analysis, $C_{25}H_{32}N_2$:
Calcd.: C, 83.28; H, 8.95; N, 7.77.
Found: C, 82.96; H, 9.05; N, 7.62.

EXPERIMENTAL EXAMPLE

1. Antihypoxic Action

Male mice (ICR/Jcl strain, 5–6 weeks old) were divided into two groups, i.e. a control group and a drug-treated group. A desiccator was decompressed to an internal pressure of 35 mmHg with a vacuum pump and, then, connected to two desiccators housing mice of the two groups, respectively. After an equilibrium was established in internal pressure among the desiccators, the time to the onset of respiratory arrest of each mouse in each group was measured and regarded as survival time. Then, taking the mean survival time in the control group as 100, the survival time of the drug-treated group was expressed in percentage (Table 7). The test drug was administered intraperitoneally 30 minutes before induction of hypoxia. The control group received physiological saline.

TABLE 7

| Compound (I) Example No.-Compound No. | 10 mg/kg | 2 mg/kg | 0.5 mg/kg | 0.1 mg/kg |
|---|---|---|---|---|
| 11-4 | 216 ± 53* | 288 ± 82* | 148 ± 17* | 116 ± 11 |
| 12 | 132 ± 8* | 163 ± 23* | 152 ± 19* | 84 ± 4 |
| 14-3 | 398 ± 95** | 137 ± 11** | 162 ± 24* | 108 ± 9 |
| 14-4 | 197 ± 32** | 188 ± 22** | 152 ± 28 | |
| 14-6 | 123 ± 6** | 143 ± 17* | 154 ± 17* | 120 ± 7* |
| 20 | | 118 ± 5* | 99 ± 5 | |
| 21-1 | 277 ± 55*** | 231 ± 59* | 155 ± 21* | 133 ± 11* |
| 21-2 | 280 ± 59*** | 147 ± 8*** | 147 ± 14** | 165 ± 26* |

*$P < 0.05$,
**$P < 0.01$,
***$P < 0.001$

2. Antiedematous Action on the Brain

Male rats (Wistar/Jcl, 11 weeks old) underwent cervical incision under ether anesthesia and the pterygopalatine artery and external carotid artery were ligated. After blockade of the common carotid artery bloodstream, a cannula was inserted retrogradely from the external carotid artery and indwelt at the origin of the internal carotid artery. Then, a suspension of carbon microspheres (50±10 μm in diameter) in 20% dextran was infused selectively into the internal carotid artery through the indwelt cannula over a period of about 10 seconds. Seventy-two hours after infusion, the brain was removed and divided into the right and left cerebral hemispheres. Then, the water, sodium and ion contents of each hemisphere were determined. The test drug was administered intraperitoneally 30 minutes before and 5 hours after infusion of the microspheres on the day of microsphere infusion and twice a day, i.e. in the morning and in the afternoon, thereafter till the end of the experiment. 5% Gum arabic was used in the control group. The results are shown in Table 8.

TABLE 8

|  | Water (%) | Na (mEq/kg) | K (mEq/kg) |
|---|---|---|---|
| Group undergoing the same operation Microspheres-treated group | 78.60 ± 0.04 | 226 ± 1 | 518 ± 2 |
| Control group | 80.35 ± 0.22 | 305 ± 19 | 488 ± 11 |
| 14-6 (dose, 50 mg × 7) | 79.36 ± 0.13** | 256 ± 5* | 506 ± 5 |
| Group undergoing the same operation Microsphere-treated group | 78.64 ± 0.05 | 225 ± 1 | 508 ± 1 |
| Control group | 80.59 ± 0.19 | 306 ± 10 | 488 ± 2 |
| 20 (dose, 5 mg × 7) | 79.80 ± 0.19* | 268 ± 8* | 499 ± 5* |

*P < 0.05,
**P < 0.01

3. Anti-Cholinesterase Action

The anti-cholinesterase action of the compound of the present invention was investigated using (acetyl-[$^3$H])-acetylcholine. Thus, the S$_1$ fraction of the cerebral cortex homogenate from male Wistar rats was used as cholinesterase source, and (acetyl-[$^3$H])-acetylcholine as the substrate and the compound of the invention as the test compound were incubated for 30 minutes and after termination of the reaction, a toluene scintillator was added. The mixture was shaken and the radioactivity of the reaction product [$^3$H]-acetic acid in the toluene layer was measured with a scintillation counter to estimate the cholinesterase-antagonizing activity.

The anticholinesterase activity of the test compound was expressed as 50% inhibitory concentration (IC$_{50}$) in Table 9.

TABLE 9

| Compound (Example No.) | Anticholinesterase activity IC$_{50}$ (μM) |
|---|---|
| 59 | 0.027 |
| 60-1 | 0.052 |
| 60-2 | 0.25 |
| 60-3 | 0.053 |
| 60-4 | 0.098 |
| 60-5 | 0.010 |
| 60-6 | 0.020 |
| 60-7 | 0.0084 |
| 60-8 | 0.15 |
| 60-10 | 0.040 |
| 60-11 | 0.032 |
| 60-12 | 0.028 |
| 60-13 | 0.048 |
| 60-14 | 0.0068 |
| 60-15 | 0.061 |
| 60-17 | 0.0061 |
| 60-19 | 0.0029 |
| 60-20 | 0.015 |
| 60-21 | 0.71 |
| 60-22 | 0.017 |
| 60-23 | 0.15 |
| 69 | 0.22 |

4. Action on Scopolamine-Induced Impairment of Spontaneous Alternation in a T-Maze The nootropic effect of the compound of the invention (Example 59) was investigated using spontaneous alternation in rats (Murray and Fibiger, Behav Neurosci. 100, 23–32, 1986) as an indicator. Nine-week-old rats were used. Feeding was restricted so that the body weight of the rat would be reduced to about 80% of free-feeding weight. Then, training was started. Training consisted of 11 trials. In the first trial one food pellet (45 mg) was placed in each of food receptacles set at ends of two arms and the rat was allowed to select either arm freely for the food reward. In the subsequent 10 trials from the second to the eleventh trial, the diet was placed only on the arm opposite to the arm which had been selected immediately before. The selection of the arm where the diet was placed was regarded as a correct response. In each acquistion trial, the rat was first placed in a home compartment and 15 seconds later the door was opened to let the animal explore freely and select either arm. The rat was brought back to the home compartment after it had ingested the pellet in the case of a correct response or after it had reached the food receptacle in the case of an incorrect response. In the experiment, the rats which had attained the correct response rate of not less than 80% were used. Scopolamine bromide was administered intraperitoneally in a dose of 0.3 mg/kg 30 minutes before the beginning of the experiment and the test compound (Example 59) was administered orally 30 minutes before scopolamine administration. The results of the experiment are expressed in correct response rate. For the analysis of significant difference between the groups, Student's t-test (two-tailed) was used. In the first experiment, groups of 7–9 rats were used, and in the second experiment, groups of 12–14 rats were used. The results are shown in Table 10 (the results in the second experiment are shown in the parentheses).

TABLE 10

| Effect on scopolamine-induced impairment of spontaneous alternation | | | |
|---|---|---|---|
| Compound | Dose (mg/kg, p.o.) | Mean correct response rate ± standard error | No. of rats |
| Physiological saline | — | 83.3 ± 1.7 | 9 |
| Physiological saline + scopolamine | — | 53.8 ± 4.6** (55.7 3.3**) | 8 (14) |
| Compound (Example 59) + scopolamine | 3 | 61.4 ± 7.1 (66.73.8+) | 7 (12) |
| Compound (Example 59) + scopolamine | 10 | 74.3 ± 3.0++ (71.73.5++) | 7 (12) |

Scopolamine was administered intraperitoneally in a dose of 0.3 mg/kg.
**P < 0.01 Compared with the physiological saline control group (t-test)
++P < 0.01 Compared with the scopolamine-treated control group (t-test)
+P < 0.05 Compared with the scopolamine-treated control group (t-test)

The compound of the invention (Example 59) dose-dependently antagonized the decrease of correct response rate by scopolamine and showed a significant ameliorative effect at 10 mg/kg.

PREPARATION EXAMPLE 1

| (1) 4-(4-Dimethylaminobenzyl)piperidine dihydrochloride (Compound of Example 20) | 50 g |
|---|---|
| (2) Lactose | 198 g |
| (3) Corn starch | 50 g |
| (4) Magnesium stearate | 2 g |

Of the above ingredients, (1) and (2) were mixed with 20 g of corn starch and the mixture was granulated using a paste prepared from 15 g of corn starch and 25 ml of water. Then, 15 g of corn starch and (4) were added and the mixture was compression-molded to give 1,000 tablets, 5 mm in diameter, each containing 50 mg of (1).

PREPARATION EXAMPLE 2

In water were dissolved 2 g of 4-(4-dimethylaminobenzyl)piperidine dihydrochloride and 1.25 g of mannitol and the solution was adjusted to pH 5-7 with 0.1N-NaOH and made up to a total of 100 ml. This solution was filtered through a 0.2 μm bacterial filter and distributed into one-hundred 1 ml-ampules.

We claim:

1. A compound which is

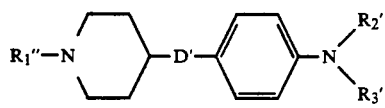

wherein $R_1''$ is hydrogen or benzyl of which the phenyl ring may be optionally substituted with from one to three substituents selected from $C_{1-3}$ alkoxy groups, $C_{1-3}$ alkyl groups, cyano, hydroxy, nitro and halogens;

D' is —$CH_2$— or —CH(OH)—; and each of $R_2'$ and $R_3'$ is independently $C_{1-6}$ alkyl or a physiologically acceptable salt thereof.

2. A compound of claim 1 wherein said benzyl contains from one to three substituents selected from the group consisting of $C_{1-3}$ alkoxy, $C_{1-3}$ alkyl, cyano, hydroxy, nitro and halogen.

3. A compound of claim 1 wherein $R_1''$ is hydrogen.

4. A compound of claim 3 wherein each of $R_2'$ and $R_3'$ is independently an unsubstituted $C_{1-6}$ alkyl.

5. A compound of claim 3 wherein D' is —$CH_2$—.

6. A compound of claim 1 wherein $R_2'$ and $R_3'$ is each methyl.

7. A compound of claim 3 wherein $R_2'$ and $R_3'$ is each methyl.

8. A compound of claim 3 which is 4-(4-dimethylaminobenzyl)piperidine fumarate.

9. A composition for the treatment of cerebral edema which comprises an effective anti-edematic amount of the compound of claim 4 and an inert pharmaceutically acceptable carrier therefor.

10. The composition of claim 9 wherein said compound is 4-(4-dimethylaminobenzyl)-piperidine fumarate.

11. A method of treating cerebral edema which comprises administering to a patent an effective amount for the treatment of said cerebral edema of a compound of claim 8.

12. A method of treating cerebral edema of claim 11 wherein said compound is 4-(4-dimethylaminobenzyl)-piperidine fumarate.

* * * * *